US009498791B2

(12) United States Patent
Otter et al.

(10) Patent No.: US 9,498,791 B2
(45) Date of Patent: Nov. 22, 2016

(54) OPPOSABLES AND AUTOMATED SPECIMEN PROCESSING SYSTEMS WITH OPPOSABLES

(71) Applicant: Ventana Medical Systems, Inc., Tucson, AZ (US)

(72) Inventors: Michael Otter, Tucson, AZ (US); Brian Howard Kram, Tucson, AZ (US);
(Continued)

(73) Assignee: VENTANA MEDICAL SYSTEMS, INC., Tucson, AZ (US)

( * ) Notice: Subject to any disclaimer, the term of this patent is extended or adjusted under 35 U.S.C. 154(b) by 569 days.

(21) Appl. No.: 13/831,255

(22) Filed: Mar. 14, 2013

(65) Prior Publication Data
US 2013/0203100 A1 Aug. 8, 2013

Related U.S. Application Data

(63) Continuation-in-part of application No. 13/509,785, filed as application No. PCT/US2010/056752 on Nov. 15, 2010, now Pat. No. 8,911,815.
(Continued)

(51) Int. Cl.
*B05C 11/02* (2006.01)
*B05D 3/12* (2006.01)
(Continued)

(52) U.S. Cl.
CPC ............ *B05C 11/028* (2013.01); *B01L 3/0293* (2013.01); *B01L 3/502* (2013.01); *B05D 3/12* (2013.01);
(Continued)

(58) Field of Classification Search
CPC .................. B05C 11/023; B05C 11/028; B01L 3/0293; Y10T 436/112499
See application file for complete search history.

(56) References Cited

U.S. PATENT DOCUMENTS 3,551,023 A 12/1970 Brackett
3,556,633 A 1/1971 Mutschmann et al.
(Continued)

FOREIGN PATENT DOCUMENTS

CN 1331810 A 1/2002
EP 0310399 A2 4/1989
(Continued)

OTHER PUBLICATIONS

English Translation of Japanese Office Action mailed Oct. 2, 2013, Japanese Patent Office, JP Patent Application No. 2012-539061 (related to present application), International Filing Date: Nov. 15, 2010, Applicant: Ventana Medical Systems, Inc., 3 pages.
(Continued)

Primary Examiner — Dah-Wei D Yuan
Assistant Examiner — Stephen Kitt
(74) Attorney, Agent, or Firm — Charney IP Law LLC; Thomas Finetti

(57) ABSTRACT

A specimen processing system is capable of processing specimens carried on slides. The specimen processing system can sequentially deliver slides and opposables to specimen processing stations. The specimen processing stations can use the opposables to apply a series of liquids to the specimens. The applied liquid can be moved along the slide using capillary action while the specimen processing stations control the processing temperatures. The applied liquid can be in a fluid-carrying gap. The opposable can contact the slide to vary a cross section of the fluid-carrying gap.

10 Claims, 19 Drawing Sheets

(72) Inventors: Carl David Martin, Oro Valley, AZ (US); Jessica Jones, Oro Valley, AZ (US); Kevin David Marshall, Tucson, AZ (US); Christine Tse, Tucson, AZ (US); Josh Harrison, Tucson, AZ (US)

Related U.S. Application Data

(60) Provisional application No. 61/261,267, filed on Nov. 13, 2009, provisional application No. 61/746,078, filed on Dec. 26, 2012, provisional application No. 61/746,085, filed on Dec. 26, 2012, provisional application No. 61/746,087, filed on Dec. 26, 2012, provisional application No. 61/746,089, filed on Dec. 26, 2012, provisional application No. 61/746,091, filed on Dec. 26, 2012.

(51) Int. Cl.
*B01L 3/02* (2006.01)
*G02B 21/34* (2006.01)
*G01N 1/31* (2006.01)
*G01N 35/00* (2006.01)
*G01N 35/10* (2006.01)
*B01L 3/00* (2006.01)

(52) U.S. Cl.
CPC ........ *G01N 1/312* (2013.01); *G01N 35/00029* (2013.01); *G01N 35/1002* (2013.01); *G02B 21/34* (2013.01); *B01L 2200/025* (2013.01); *B01L 2300/0822* (2013.01); *B01L 2300/0877* (2013.01); *G01N 2035/00138* (2013.01); *G01N 2035/00534* (2013.01); *G01N 2035/1037* (2013.01); *Y10T 436/112499* (2015.01)

(56) References Cited

U.S. PATENT DOCUMENTS

| | | |
|---|---|---|
| 3,672,745 A | 6/1972 | Speelman |
| 3,961,346 A | 6/1976 | White |
| 3,972,423 A | 8/1976 | Tipton |
| 3,985,096 A | 10/1976 | Guimbretiere |
| 4,023,949 A | 5/1977 | Schlom et al. |
| 4,107,940 A | 8/1978 | Schlom et al. |
| 4,146,414 A | 3/1979 | Stormby |
| 4,156,351 A | 5/1979 | Schlom et al. |
| 4,203,797 A | 5/1980 | Stormby |
| 4,336,765 A | 6/1982 | Coughlin |
| 4,359,013 A | 11/1982 | Prevo |
| 4,392,450 A | 7/1983 | Prevo |
| 4,418,527 A | 12/1983 | Schlom et al. |
| 4,428,793 A | 1/1984 | Sato et al. |
| 4,597,982 A | 7/1986 | Delameter |
| 4,731,335 A | 3/1988 | Brigati |
| 4,777,020 A | 10/1988 | Brigati |
| 4,790,640 A | 12/1988 | Nason |
| 4,801,431 A | 1/1989 | Cuomo et al. |
| 4,849,340 A | 7/1989 | Oberhardt |
| 4,911,782 A | 3/1990 | Brown |
| 5,002,736 A | 3/1991 | Babbitt et al. |
| 5,023,187 A | 6/1991 | Koebler et al. |
| 5,075,079 A | 12/1991 | Kerr et al. |
| 5,188,963 A | 2/1993 | Stapleton |
| 5,256,241 A | 10/1993 | Noever |
| 5,273,905 A | 12/1993 | Muller et al. |
| 5,281,516 A | 1/1994 | Stapleton et al. |
| 5,338,358 A | 8/1994 | Mizusawa et al. |
| 5,503,803 A | 4/1996 | Brown |
| 5,527,510 A | 6/1996 | Atwood et al. |
| 5,580,414 A | 12/1996 | Ljungmann |
| 5,650,332 A | 7/1997 | Gao et al. |
| 5,658,723 A | 8/1997 | Oberhardt |
| 5,681,741 A | 10/1997 | Atwood et al. |
| 5,812,312 A | 9/1998 | Lorincz |
| 5,830,028 A | 11/1998 | Zovko et al. |
| 5,985,669 A * | 11/1999 | Palander ............ B01F 11/0042 422/523 |
| 5,989,386 A | 11/1999 | Elliott |
| 6,037,168 A | 3/2000 | Brown |
| 6,083,759 A | 7/2000 | Teshima |
| 6,146,592 A | 11/2000 | Kawashima et al. |
| 6,180,314 B1 | 1/2001 | Berndt |
| 6,197,494 B1 | 3/2001 | Oberhardt |
| 6,239,906 B1 | 5/2001 | Lorincz |
| D445,909 S | 7/2001 | Pogorzelski |
| 6,258,322 B1 | 7/2001 | Meikle |
| 6,302,985 B1 | 10/2001 | Takahashi et al. |
| 6,358,475 B1 | 3/2002 | Berndt |
| 6,382,693 B1 | 5/2002 | Ljungmann |
| 6,385,987 B2 | 5/2002 | Schlom et al. |
| 6,395,536 B2 | 5/2002 | Freeman |
| 6,403,931 B1 | 6/2002 | Showalter et al. |
| D464,141 S | 10/2002 | McMenamy et al. |
| 6,474,386 B2 | 11/2002 | Takahashi et al. |
| 6,485,918 B1 * | 11/2002 | Schermer ............ B01F 11/0045 366/267 |
| 6,486,947 B2 | 11/2002 | Modlin et al. |
| 6,544,395 B1 | 4/2003 | Merchant et al. |
| 6,544,793 B2 | 4/2003 | Berndt |
| 6,544,798 B1 | 4/2003 | Christensen et al. |
| 6,567,214 B2 | 5/2003 | Lorincz |
| 6,568,447 B1 | 5/2003 | Sakai et al. |
| 6,589,650 B1 | 7/2003 | Govek et al. |
| 6,626,224 B1 | 9/2003 | Ljungmann |
| 6,703,247 B1 | 3/2004 | Chu |
| 6,717,657 B2 | 4/2004 | Berndt |
| D495,806 S | 9/2004 | Norholm |
| 6,796,353 B2 | 9/2004 | Lang et al. |
| 7,063,758 B2 | 6/2006 | Sakayori et al. |
| 7,186,383 B2 | 3/2007 | Webster et al. |
| 7,271,006 B2 | 9/2007 | Reinhardt et al. |
| 7,300,804 B2 | 11/2007 | Sellek-Prince |
| D569,990 S | 5/2008 | Fisch |
| 7,378,055 B2 | 5/2008 | Lemme et al. |
| 7,425,306 B1 | 9/2008 | Kram |
| 7,468,160 B2 | 12/2008 | Thompson et al. |
| 7,468,161 B2 | 12/2008 | Reinhardt et al. |
| 7,470,541 B2 | 12/2008 | Copeland et al. |
| 7,615,371 B2 | 11/2009 | Kram |
| 7,820,381 B2 | 10/2010 | Lemme et al. |
| D645,971 S | 9/2011 | Taylor et al. |
| 8,911,815 B2 | 12/2014 | Kram et al. |
| D728,120 S | 4/2015 | Kram et al. |
| 2002/0182115 A1 | 12/2002 | Aghassi et al. |
| 2003/0087292 A1 | 5/2003 | Chen et al. |
| 2003/0203493 A1 | 10/2003 | Lemme et al. |
| 2003/0211630 A1 | 11/2003 | Richards et al. |
| 2003/0231987 A1 | 12/2003 | Carmack et al. |
| 2004/0023371 A1 | 2/2004 | Fawcett |
| 2004/0082058 A1 | 4/2004 | Schleifer et al. |
| 2004/0092024 A1 | 5/2004 | Reinhardt et al. |
| 2005/0089949 A1 | 4/2005 | Baer et al. |
| 2005/0153453 A1 | 7/2005 | Copeland et al. |
| 2005/0164374 A1 | 7/2005 | Kram |
| 2005/0186114 A1 | 8/2005 | Reinhardt et al. |
| 2005/0270642 A1 | 12/2005 | McLellan et al. |
| 2006/0019302 A1 * | 1/2006 | Lemme ................ B01L 3/0293 435/6.16 |
| 2006/0035369 A1 | 2/2006 | Gauer et al. |
| 2006/0051253 A1 | 3/2006 | Gausepohl |
| 2006/0105462 A1 | 5/2006 | Sellek-Prince |
| 2006/0120921 A1 | 6/2006 | Elliot et al. |
| 2006/0148063 A1 | 7/2006 | Fauzzi et al. |
| 2006/0166371 A1 | 7/2006 | Testa et al. |
| 2007/0039435 A1 | 2/2007 | Kokubo |
| 2008/0050511 A1 | 2/2008 | Sellek-Prince |
| 2009/0004691 A1 | 1/2009 | Erickson et al. |
| 2010/0031757 A1 | 2/2010 | Hoyer |
| 2011/0217731 A1 | 9/2011 | Burgart et al. |
| 2011/0305842 A1 | 12/2011 | Kram |

(56) References Cited

U.S. PATENT DOCUMENTS

2013/0052331 A1 2/2013 Kram et al.
2015/0071833 A1 3/2015 Kram et al.

FOREIGN PATENT DOCUMENTS

| | | |
|---|---|---|
| EP | 0334534 A2 | 9/1989 |
| EP | 0502108 A1 | 9/1992 |
| EP | 0611598 A2 | 8/1994 |
| EP | 0801732 A1 | 10/1997 |
| GB | 1562643 A | 3/1980 |
| JP | 7043278 | 2/1995 |
| JP | H09-043118 A | 2/1997 |
| JP | H09-170973 A | 6/1997 |
| JP | 2000508423 A | 7/2000 |
| JP | 2005530208 A | 10/2005 |
| JP | 2008507701 A | 3/2008 |
| JP | 2008537149 A | 9/2008 |
| WO | WO-93/19207 A1 | 9/1993 |
| WO | WO-9520176 A1 | 7/1995 |
| WO | WO-96/21142 A1 | 7/1996 |
| WO | WO-97/09616 A1 | 3/1997 |
| WO | 9726541 | 7/1997 |
| WO | WO-99/34190 A1 | 7/1999 |
| WO | 9949295 | 9/1999 |
| WO | WO-9944030 | 9/1999 |
| WO | WO-2005064309 A1 | 7/2005 |
| WO | WO-2006012498 | 2/2006 |
| WO | WO-2006055096 A2 | 5/2006 |
| WO | 2010074915 | 7/2010 |
| WO | 2010074917 | 7/2010 |
| WO | 2011002779 | 1/2011 |
| WO | WO-2011060387 A1 | 5/2011 |
| WO | 2011139978 | 11/2011 |
| WO | 2013127990 | 9/2013 |
| WO | 2014102160 | 7/2014 |
| WO | 2014102161 | 7/2014 |
| WO | 2014102183 | 7/2014 |
| WO | 2014105739 | 7/2014 |
| WO | 2014105744 | 7/2014 |

OTHER PUBLICATIONS

International Search Report and Written Opinion for Application No. PCT/US2010/056752 (related to present application); Applicant: Ventana Medical Systems, Inc. et al; Date of Mailing: Apr. 29, 2011 (6 pages).
International Searching Authority: European Patent Office; International Search Report for PCT Application No. PCT/EP2013/077648 (counterpart to present application), Applicant: Ventana Medical Systems, Inc., Date of Mailing: Sep. 16, 2014, 4 pages.

* cited by examiner

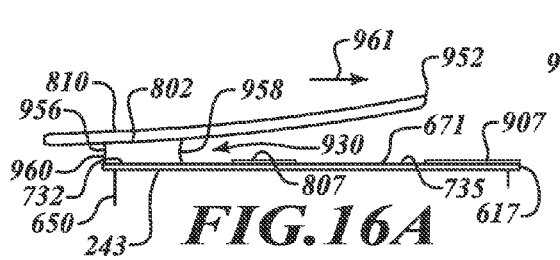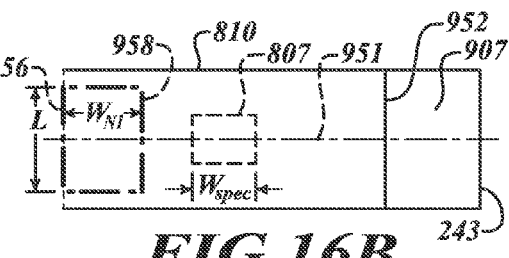
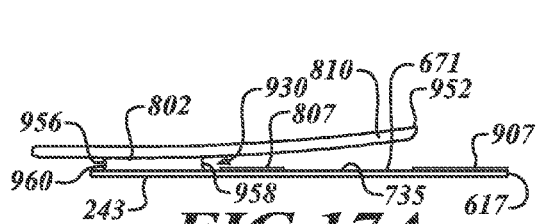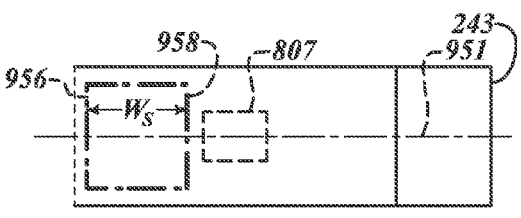
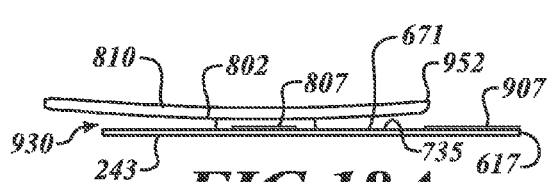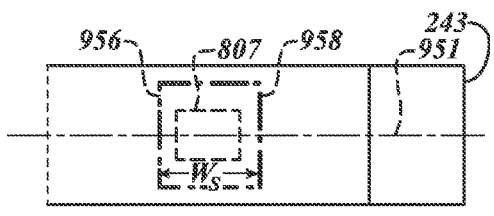
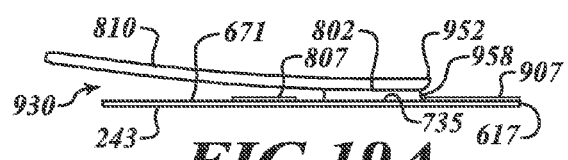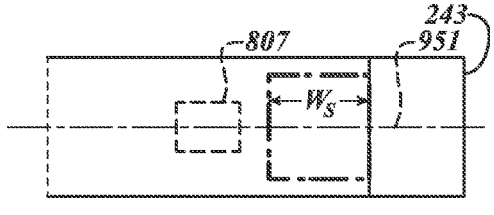
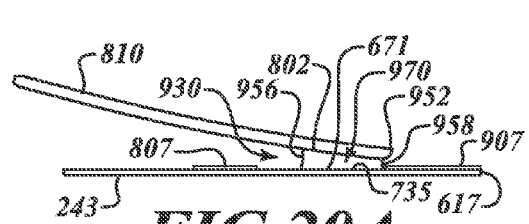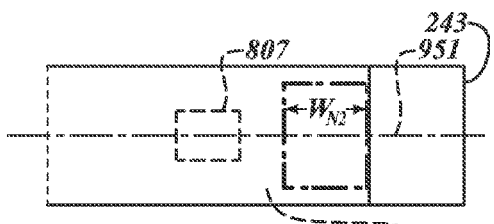

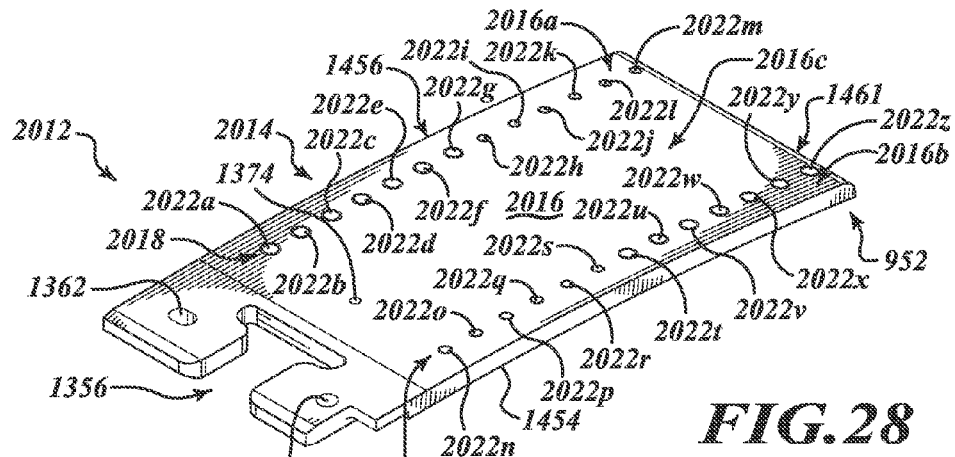
FIG.28
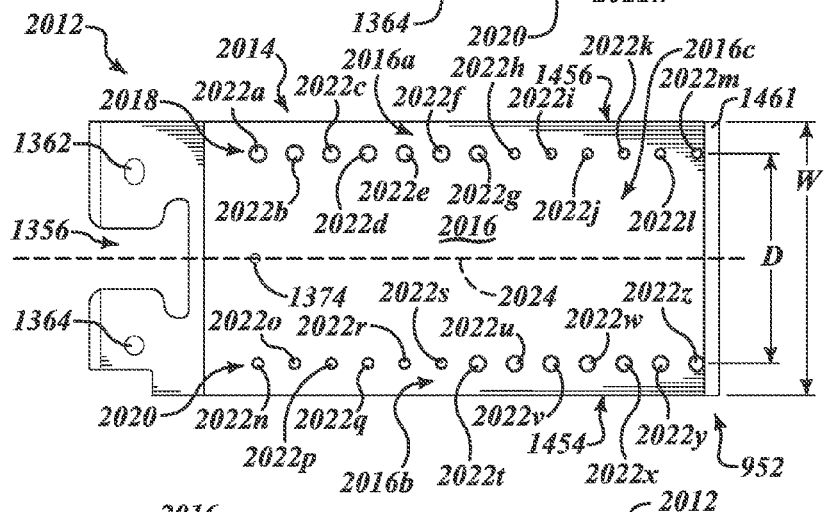
FIG.29
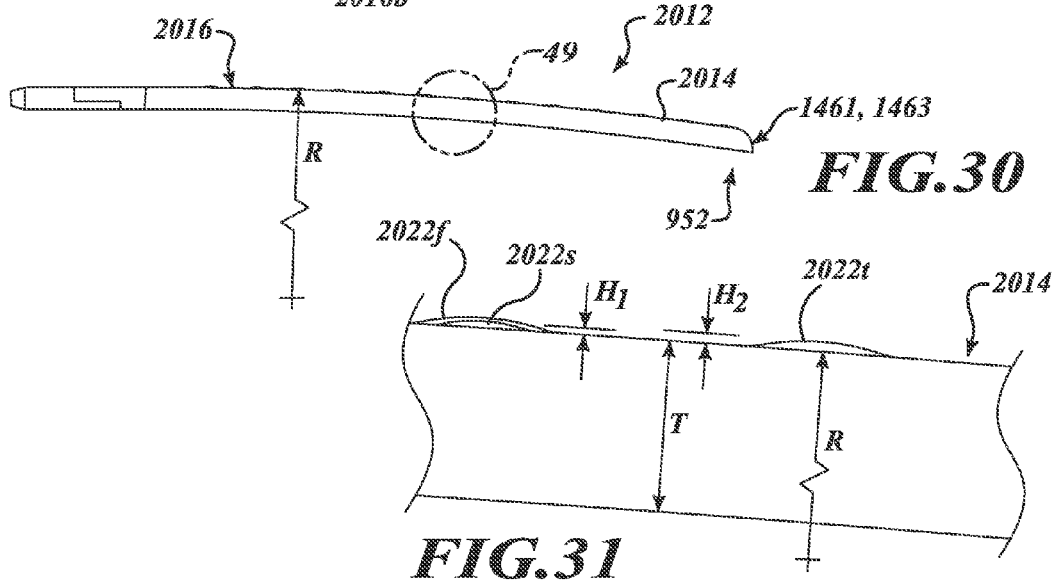
FIG.30
FIG.31

OPPOSABLES AND AUTOMATED SPECIMEN PROCESSING SYSTEMS WITH OPPOSABLES

CROSS REFERENCE TO RELATED APPLICATIONS

This application is a continuation-in-part of U.S. application Ser. No. 13/509,785 filed Nov. 12, 2012 (U.S. Pat. No. 8,911,815) and entitled "THIN FILM PROCESSING APPARATUSES FOR ADJUSTABLE VOLUME ACCOMMODATION," which is a U.S. National Phase application of PCT/US2010/056752, filed Nov. 15, 2010, which claims the benefit under 35 U.S.C. §119(e) of U.S. Provisional Patent Application No. 61/261,267 filed on Nov. 13, 2009 and the present application claims the benefit under 35 U.S.C. §119(e) of U.S. Provisional Patent Application No. 61/746,078, filed on Dec. 26, 2012; U.S. Patent Application No. 61/746,085, filed on Dec. 26, 2012 and entitled "AUTOMATED SPECIMEN PROCESSING SYSTEMS AND METHODS OF USING THE SAME"; U.S. Patent Application No. 61/746,087, filed on Dec. 26, 2012 and entitled "SPECIMEN PROCESSING SYSTEMS AND METHODS FOR MODERATING EVAPORATION", U.S. Patent Application No. 61/746,089, filed on Dec. 26, 2012 and entitled "SPECIMEN PROCESSING SYSTEMS AND METHOD FOR UNIFORMLY HEATING SLIDES"; and U.S. Patent Application No. 61/746,091, filed on Dec. 26, 2012 and entitled "SPECIMEN PROCESSING SYSTEMS AND METHODS FOR ALIGNING SLIDES". All applications listed above are incorporated herein by reference in their entireties.

TECHNICAL FIELD

This disclosure relates to systems for treating specimens carried on microscope slide for analysis. In particular, the disclosure relates to microscope slide carrying specimen processing systems and methods of processing such specimens.

BACKGROUND

A wide variety of techniques have been developed to prepare and analyze biological specimens. Example techniques include microscopy, microarray analyses (e.g., protein and nucleic acid microarray analyses), and mass spectrometric methods. Specimens are prepared for analysis by applying one or more liquids to the specimens. If a specimen is treated with multiple liquids, both the application and the subsequent removal of each of the liquids can be important for producing samples suitable for analysis.

Microscope slides bearing biological specimens, e.g., tissue sections or cells, are often treated with one or more dyes or reagents to add color and contrast to otherwise transparent or invisible cells or cell components. Specimens can be prepared for analysis by manually applying dyes or other reagents to specimen-bearing slides. This labor-intensive process often results in inconsistent processing due to individual techniques among laboratory technicians.

"Dip and dunk" automated machines immerse specimens in liquids by a technique similar to manual immersing techniques. These automated machines can process specimens in batches by submerging racks carrying microscope slides in open baths. Unfortunately, carryover of liquids between containers leads to contamination and degradation of the processing liquids. Worse, cells sloughing of the specimen carrying slides can cause contamination of other slides in the liquid baths. These types of processes also utilize excessive volumes of liquids, resulting in relatively high processing costs when the reagents must be changed to reduce the possibility of specimen cross-contamination. Open containers are also prone to evaporative losses and reagent oxidative degradation that may significantly alter the concentration and effectiveness of the reagents, resulting in inconsistent processing. It may be difficult to process samples without producing significant volumes of waste that may require special handling and disposal.

Immunohistochemical and in situ hybridization staining processes are often used to prepare tissue specimens. The rate of immunohistochemical and in situ hybridization staining of sectioned fixed tissue on a microscope slide is limited by the speed at which molecules (e.g., conjugating biomolecules) can diffuse into the fixed tissue from an aqueous solution placed in direct contact with the tissue section. Tissue is often "fixed" immediately after excision by placing it in a 10% solution of formaldehyde, which preserves the tissue from autocatalytic destruction by cross-linking much of the protein via methylene bridges. This cross-linked tissue may present many additional barriers to diffusion, including the lipid bilayer membranes that enclose individual cells and organelles. Conjugate biomolecules (antibody or DNA probe molecules) can be relatively large, ranging in size from a few kilodaltons to several hundred kilodaltons, which constrains them to diffuse slowly into solid tissue with typical times for sufficient diffusion being in the range of several minutes to a few hours. Typical incubation conditions are 30 minutes at 37 degrees centigrade. The stain rate is often driven by a concentration gradient so the stain rate can be increased by increasing the concentration of the conjugate in the reagent to compensate for slow diffusion. Unfortunately, conjugates are often very expensive, so increasing their concentration is wasteful and often not economically viable. Additionally, the excessive amount of conjugate that is driven into the tissue, when high concentrations are used, is entrapped in the tissue, is difficult to rinse out, and causes high levels of non-specific background staining. In order to reduce the noise due to non-specific background staining and increase the signal of specific staining, low concentrations of conjugate with long incubation times are often used to allow the conjugate to bind only to the specific sites.

Histology staining instruments often use relatively large volumes of reagent (100 µL) in a puddle of typically 300 µL of buffer. Some conventional instruments mix the reagent by alternating tangential air jets onto an overlaying oil layer that rotates and counter-rotates when contacted by the alternating air jets, thereby imparting motion into the underlying aqueous puddle. This mixing is slow and not particularly vigorous, and it can create significant evaporation losses, especially at the elevated temperatures that are often necessary. Large volumes of rinse liquid are used to physically displace the large puddles of reagents, which are covered with oil. This rinsing procedure produces large volumes of waste liquid, which may be hazardous waste.

OVERVIEW OF TECHNOLOGY

At least some embodiments of the technology are directed to biological specimen processing systems capable of processing specimens carried on slides. The specimen processing systems can sequentially deliver slides and opposing surfaces (opposables) to specimen processing stations. The specimen processing stations can use opposables to manipulate and direct a series of liquids to the specimens. The liquids can be manipulated over or across the slide surfaces in conjunction with capillary action while the specimen processing stations control the movement of the opposables and the processing temperatures for histology staining, immunohistochemical staining, in situ hybridization staining, or other specimen processing protocols. In some embodiments, the opposables are surfaces or opposable elements capable of manipulating one or more substances on a slide. Manipulating a substance in the form of a fluid can include spreading the fluid, displacing a thin film of fluid, or otherwise altering a bolus of fluid, a band of fluid, or a thin film.

At least some embodiments of the technology are directed to a system that contacts a biological specimen with a liquid by moving an opposable in contact with the liquid. A distance separating a non-planar (e.g., curved), wetted surface of the opposable and a slide carrying the specimen is sufficient to form a liquid meniscus layer between the wetted surface and the slide. The meniscus layer contacts at least a portion of the biological specimen and is moved across the slide using capillary and other manipulative action.

The meniscus layer, in some embodiments, can be a relatively thin fluid film, a band of fluid, or the like. The opposable is movable to different positions relative to the slide and can accommodate different volumes of liquid forming the meniscus layer. The capillary action can include, without limitation, movement of the meniscus layer due to the phenomenon of the liquid spontaneously creeping through the gap between the curved, wetted opposable surface and the slide due to adhesive forces, cohesive forces, and/or surface tension. The opposable can manipulate (e.g., agitate, displace, etc.) the liquid to process the specimen using relatively small volumes of a liquid to help manage waste and provide consistent processing. Evaporative losses, if any, can be managed to maintain a desired volume of liquid, reagent concentration, or the like. Relatively low volumes of liquids can be used to process the specimens for a reduced liquid waste.

In some embodiments, a system includes one or more automated slide holders that can heat individual slides via conduction to produce temperature profiles across slides that compensate for heat losses. The heat losses can be caused by evaporation of liquid in a gap between a slide and an opposable disposed proximate to the slide. In one embodiment, the slide holder has a slide support surface and produces a non-uniform temperature profile along the slide support surface contacting the slide such that a specimen-bearing surface of the slide has a substantially uniform temperature profile when the slide is located on the slide support surface. In some embodiments, a non-uniform temperature profile is produced across the slide support surface while a substantially uniform temperature profile is produced along the mounting surface of the slide. Another feature of at least some embodiments of the present technology is that the slide holder can be configured to produce a low temperature heating zone and a high temperature heating zone surrounding the low temperature heating zone. The high temperature zone can compensate for relative high evaporative heat losses to keep the specimen at a generally uniform temperature.

In some embodiments, a slide processing apparatus for processing a specimen carried by a slide includes a staining module. The staining module includes a slide holder platen, an opposable element, and an opposable actuator. The slide holder platen has a first sidewall, a second sidewall, and a slide receiving region between the first and sidewall. A slide is positioned on the slide receiving region. The slide includes a first edge and an opposing second edge. The opposable actuator holds an opposable element having a first and a second edge portion to form a capillary gap between the opposable element and the slide. The first edge portion of the opposable element is closer to the first edge of the slide, while the second edge portion of the opposable element is closer to the second edge of the slide.

The slide processing apparatus, in some embodiments, includes one or more dispensers positioned to deliver a supplemental liquid between the opposable element the slide while a liquid is held in the gap there between. Additionally, the slide processing apparatus can include a controller communicatively coupled to the dispenser(s) and programmed to command the dispenser such that the dispenser delivers the supplemental liquid to keep a volume of liquid between the opposable element and the slide within an equilibrium volume range. In some embodiments, the controller is programmed to deliver supplemental liquid at a predetermined rate. In one embodiment, the predetermined rate is equal to or less than about 7 µL per minute. The rate can be selected based on the specimen staining protocol being processed.

The slide processing apparatus, in some embodiments, further comprises a plurality of additional staining modules and a controller configured to independently control each of the staining modules. The staining modules can use disposable or reusable opposable elements (opposables) to spread and move reagents across the specimens.

The first edge portion of the opposable element can extend to or beyond the first edge of the slide and the second edge portion of the opposable element can extend to or beyond the opposite edge of the slide. The opposable element can include a mounting end having at least one slot dimensioned to be received and retained by at least a portion of the opposable actuator. In some embodiments, the opposable element has a captivation end and an arcuate main body extending from the captivation end. The arcuate main body is configured to roll along or above the slide to move a liquid across the surface of the slide. The captivation end has a radius of curvature equal to or less than about 0.08 inch. Other dimensions can also be used.

The opposable element can include a first and a second slide contact surface located proximate to each opposable element edge portion respectively. Such slide contact surfaces can comprise intermittent slide contact surfaces with spaces therebetween to enable fluid to pass therethrough.

The staining module can include at least one heating element positioned to conductively heat the first sidewall, the second sidewall, or both. The opposable actuator is moveable to roll a curved portion of the opposable element along or above the slide to move a band of a liquid across at least a portion of the slide carrying a specimen. The slide holder can be used to heat the slide, specimen, and/or liquid while the band of liquid is manipulated across the specimen.

In some embodiments, a system for processing a specimen carried by a slide comprises a specimen processing station and a controller. The specimen processing station includes an opposable actuator and a slide holder platen. The slide holder platen includes a slide support region and a liquid replenishment device. The slide holder platen is configured to heat a liquid on a slide at the slide support region while an opposable element held by the opposable actuator contacts and moves the liquid across the slide surface. The replenishment device is configured to deliver a supplemental liquid between the opposable element and the slide. The controller is programmed to control the specimen processing station such that the replenishment device delivers the supplemental liquid at a replenishing rate to compensate for evaporative losses of the liquid.

The controller, in some embodiments, includes one or more memories and a programmable processor. The memory stores a first sequence of program instructions and a second sequence of program instructions. The programmable processor is configured to execute the first sequence of program instructions in order to process a specimen on the slide with a first liquid and configured to execute the second sequence of program instructions to process the specimen with a second liquid that is different from the first liquid. In some embodiments, the programmable processor is configured to execute the first sequence of program instructions in order to heat the slide to a first temperature using the slide holder platen, and the controller is configured to execute the second sequence of program instructions in order to heat the slide to a second temperature using the slide platen, the second temperature is different from the first temperature.

The controller, in some embodiments, is configured to execute a first sequence of program instructions to command the replenishment device to deliver a first liquid to the slide at a first rate. The controller is further configured to execute a second sequence of program instructions to command the replenishment device to deliver a second liquid to the slide at a second rate that is different from the first rate. In certain embodiments, the first rate corresponds to an evaporation rate of the first liquid, and the second rate corresponds to an evaporation rate of the second liquid. The controller can help moderate evaporative losses.

The controller, in some embodiments, includes a memory that stores a replenishment program executable by the controller in order to keep a volume of the liquid on the slide within an equilibrium volume range. In certain embodiments, the equilibrium volume range is about 70 μL to about 200 μL. In certain embodiments, the controller is programmed to command the specimen processing station to keep a volume of the liquid between a maximum equilibrium volume corresponding to an over-wetting condition and a minimum equilibrium volume corresponding to an under-wetting condition. The controller, in some embodiments, is programmed to command the specimen processing station to move a volume of the liquid across a specimen held on the slide by moving an opposable element held by the opposable actuator relative to the slide and can also be programmed to deliver the supplemental liquid from the replenishment device to generally compensate for a decrease in the volume of the liquid due to evaporation.

The controller, in some embodiments, is configured to receive reference evaporation rate information (e.g., evaporation rate information for the liquid) from a memory and to control the specimen processing station based on the reference evaporation rate information. Additionally or alternatively, the controller can be programmed to command the specimen processing station such that the replenishment device provides the supplemental liquid at a rate selected based on an evaporation rate of the liquid.

The system for processing a specimen, in some embodiments, further comprises an opposable element and a controller. The opposable element is held by the opposable actuator and can extend outwardly past edges of the slide. The controller is programmed to control the specimen processing station to move the opposable element while the opposable element manipulates the liquid across the slide while an evaporation rate of the liquid is kept equal to or less than about a predetermined rate (e.g., 7 μL per minute, 5 μL per minute, or the like).

The slide holder platen, in some embodiments, includes a heating element that receives electrical energy and outputs thermal energy to heat the slide via conduction. The heating element can include one or more resistive heating elements.

In some embodiments, a method of processing a specimen carried by a slide comprises heating a liquid on a slide held by a slide holder. The opposable element is rolled to contact the liquid on the slide and to move the liquid across a biological specimen on the slide. A replenishing rate is determined based on an evaporation rate of the liquid. A supplemental liquid is delivered based on the replenishing rate to substantially compensate for evaporative losses of the liquid. The opposable element, which contacts the liquid comprising the supplemental liquid, is rolled so as to repeatedly contact the specimen with the liquid.

The volume of the supplemental liquid delivered onto the slide can be equal to or greater than a decrease in the volume of the liquid via evaporation. Additionally or alternatively, the supplemental liquid can be delivered onto the slide by delivering the supplemental liquid to keep a volume of the liquid on the slide equal to or greater than a minimum equilibrium volume and at or below a maximum equilibrium volume. Additionally or alternatively, the supplemental liquid can be delivered onto the slide while the opposable element rolls along the slide.

In some embodiments, a method of processing a specimen on a slide includes moving a liquid along a slide using an opposable element contacting the liquid. The temperature of the liquid on the slide is controlled while moving the liquid. At least one of a volume of the liquid and/or a total evaporation rate of the liquid is evaluated, and a supplemental liquid is delivered onto the slide based on the evaluation to keep the volume of the liquid on the slide within an equilibrium volume range. In certain embodiments, the volume of the liquid and the total evaporation rate of the liquid and be received from a memory to evaluate the volume of the liquid and the total evaporation rate of the liquid from a memory evaluating the at least one of the volume of the liquid and/or the total evaporation rate of the liquid includes receiving. The equilibrium volume range can be about 125 μL to about 175 μL.

In some embodiments, a slide processing apparatus comprises a slide holder platen and an opposable actuator. The slide holder platen has a receiving region configured to receive a slide with a first side of the slide facing the receiving region and a second side facing away from the receiving region. The opposable actuator is positioned to hold an opposable element to define a capillary gap between the opposable element and a slide surface located at the receiving region. The opposable actuator is configured to advance the capillary gap in a first direction along the slide to move a band of liquid across the length and width of the second side of the slide from a first position to a second position.

The opposable actuator, in some embodiments, is configured to alternatingly roll the opposable element along the slide in the first direction and a second direction opposite the first direction to manipulate the band of liquid across the surface of the slide between the first position and the second position. The band of liquid at the first position is between an end of the opposable element and the slide, and the band of liquid at the second position is between the opposable element and an end of the slide. The band of liquid can be narrowed at each of the first position and the second position prior to moving the band of liquid to the other of the first position and second position. The opposable actuator, in some embodiments, is a variable bandwidth compression opposable actuator configured to decrease the width of the band a predetermined amount. The predetermined amount can be selected by a controller or an operator.

The opposable actuator, in some embodiments, is configured to move the opposable element relative to the slide to reduce the width of the band of liquid at an end of an opening defined by an end of at least one of the slide and/or the opposable element by at least 50%, 40%, or 25%. Additionally or alternatively, the opposable actuator can be configured to move the opposable element to displace the band of liquid between the first position and the second position while maintaining the latitudinal width of the band of liquid. The opposable actuator, in some embodiments, is moveable between a first configuration in which the band of liquid is narrowed at a first end of an opening between the opposable element and an end of the slide and a second configuration in which the band of liquid is narrowed at a second end of the opening. The opposable actuator, in some embodiments, is movable to an over-roll configuration to move a first side of the band of liquid towards a second side of the band of liquid to decrease the width of the band of liquid while the second side of the band of liquid is held substantially stationary at an end of one of the opposable element and the slide.

The slide processing apparatus, in some embodiments, further comprises a staining module and a controller. The staining module comprises the slide holder platen and the opposable actuator. The controller is communicatively coupled to the staining module. The controller is programmed to command the staining module to move the opposable element to move the capillary gap.

The slide processing apparatus, in some embodiments, further comprises an opposable element including a mounting end held by an opposable receiver of the opposable actuator, a captivating end opposite the mounting end, and a main body. The main body is between the mounting end and the captivating end. The captivating end cooperates with the slide to accumulate the liquid at an end of a mounting surface of the slide proximate to a label on the slide as the mounting end is moved away from the slide.

The slide processing apparatus, in some embodiments, further comprises an opposable element having a tapered end facing the receiving region. The tapered end is positioned to contact and captivate the band of liquid. In certain embodiments, the tapered end includes a rounded region extending between opposite longitudinally extending edges of the opposable element.

The opposable actuator, in some embodiments, has a rolling state to roll the opposable element along the slide to move the band of liquid from a location at an end of an opening defined by an end of the slide and the opposable element to a location at an opposing end of the opening. The opposable actuator can have a static state to keep the opposable element stationary relative to the slide to perform, for example, incubation.

The slide processing apparatus, in some embodiments, further comprises a slide supported by a contact surface of the receiving region such that the slide extends laterally outward past opposing edges of the contact surface. The slide can carry one or more specimens.

The slide processing apparatus, in some embodiments, further comprises an opposable element held by the opposable actuator. The opposable element has a curved captivation end. The captivation end can have a radius of curvature equal to or less than about 0.08 inch. In certain embodiments, the opposable element has an arcuate body for rolling along the slide at the receiving region.

In some embodiments, a slide processing apparatus comprises a slide holder platen and an opposable actuator. The opposable actuator includes an opposable receiver and a drive mechanism. The opposable receiver is positioned to hold an opposable element and to form a capillary gap between the opposable element and a slide held by the slide holder platen when in an activation position. The drive mechanism has a rolling state for rolling the opposable element in a first direction along the slide to move a band of liquid to an end of a space between the opposable element and the slide. The drive mechanism has an over-rolling state for rolling the opposable element in the first direction to decrease a width of the band of liquid captivated at the end of the space.

The opposable actuator, in some embodiments, is configured to move the opposable element to move the band of liquid across at least most of a mounting surface of the slide. The width of the band of liquid can be decreased by moving at least a portion of the opposable element away from the slide. The width of the band of liquid is in a direction substantially parallel to a longitudinal axis of the slide.

In some embodiments, a method for processing a specimen carried by a slide comprises delivering a slide and an opposable element to a staining module. The opposable element held by the staining module is positioned relative to the slide held by the staining module to hold a liquid in a capillary gap between the slide and the opposable element. The opposable element is moved relative to the slide to displace the liquid in a first direction that is substantially parallel to the longitudinal axis of the slide and towards an end of an opening between the slide and the opposable element. The opposable element is moved relative to the slide to reduce a width of a band of the liquid in the first direction while the band of liquid is captivated at the end of the opening.

The band of liquid, in some embodiments, is alternatingly moved between the end of the opening and an opposing end of the opening by rolling the opposable element along the slide in the first direction and a second direction opposite the first direction. The opposable element can include one or more gapping elements for maintaining spacing between a main body of the opposable element and the slide.

The band of liquid, in some embodiments, is spread to increase the width of the band of liquid. The spread band of liquid can be moved across a specimen on the slide. In certain embodiments, the width of the band of liquid is reduced at one end of the capillary gap prior to moving the band of liquid to the other end of the gap.

The method for processing the specimen, in some embodiments, further comprises captivating substantially all of the liquid at the end of the gap while reducing the width of the band of liquid.

The method for processing the specimen, in some embodiments, further comprises displacing the band of liquid across a specimen on the slide while maintaining the width of the band of liquid.

The method for processing the specimen, in some embodiments, further comprises reducing the width of the band of liquid by at least 50% by moving the opposable element relative to the slide. A volume of the liquid can be equal to or greater than about 75 µL.

The width of the band of liquid, in some embodiments, is less than a length of the band of the liquid. The width of the band of liquid is substantially parallel to the longitudinal axis of the slide. The length of the band of liquid is substantially perpendicular to the longitudinal axis of the slide.

In some embodiments, a slide heating apparatus comprises a support element and a heater. The support element has a support surface configured to support a slide with a back side of the slide facing the support surface and a specimen-bearing surface of the slide opposite the back side of the slide. The heater is coupled to the support element. The slide heating apparatus is configured to deliver thermal energy non-uniformly across the support surface to the back side of the slide via conduction to substantially compensate for non-uniform heat losses associated with evaporation of a liquid on the specimen-bearing surface.

The heater, in some embodiments, is positioned to deliver heat to the slide via the support element to produce a substantially uniform temperature profile along a specimen-bearing portion of the specimen-bearing surface. In some embodiments, the substantially uniform temperature profile has less than a 5% temperature variation across the specimen-bearing portion of the specimen-bearing surface. In some embodiments, the substantially uniform temperature profile has less than a 4° C. temperature variation across the specimen-bearing surface. Other temperature profiles can also be achieved.

The heater, in some embodiments, includes at least two spaced apart elongate portions for conductively heating side portions of the support surface and two end heating portions of the support surface extending between the elongate portions. The two end heating portions are positioned to heat both a portion of the support surface for contacting an end of the slide and a portion of the support surface for contacting a region of the slide adjacent to a label of the slide.

The slide heating apparatus, in some embodiments, is configured to produce a low heating zone along a central region of the support surface and a high heating zone along the support surface. The high heating zone can surround (e.g., circumferentially surround) the low heating zone.

The slide heating apparatus, in some embodiments, further comprises a convection assembly positioned to produce a convective flow that passes through a pocket defined by the heater to cool the support element. In some embodiments, the convection assembly includes one or more fans. The convective flow can cool the support element without flowing across the specimen on the slide.

The slide heating apparatus, in some embodiments, further comprises a pair of sidewalls each having a thermally conductive portion and an insulating portion. The thermally conductive portion facing the slide to heat the slide.

The slide heating apparatus, in some embodiments, further comprises an overmolded holder comprising an insulating material. The support element is positioned between and supported by sidewalls of the overmolded holder. The insulating material can have a thermal conductivity that is less than a thermal conductivity of a material of the support element. In some embodiments, the insulating material comprises a non-metal material (e.g., plastic) and the support element comprises metal.

In some embodiments, at least one of the heater and the support element comprises mostly stainless steel by weight. In some embodiments, the support surface comprises stainless steel. In some embodiments, most of the support element between the support surface and the heater is stainless steel. The portion of the support element between the slide and the heater can have a thermal conductivity equal to or less than about 20 W/m*K.

In some embodiments, a method for heating a biological specimen carried on a slide includes positioning a slide on a support element of a conductive slide heating apparatus such that a back side surface of the slide faces the support element and a specimen-bearing surface of the slide faces away from the support element. Heat can be delivered non-uniformly across the back side surface of the slide via the support element to substantially compensate for evaporative heat losses associated with evaporation of a liquid on the specimen-bearing surface. The evaporative heat losses are non-uniform across the specimen-bearing surface of the slide.

A non-uniform temperature profile, in some embodiments, can be produced along a support surface of the support element contacting the back side surface of the slide such that the specimen-bearing surface has a temperature profile that is more uniform than the non-uniform temperature profile. In some embodiments, a temperature variation (e.g., a temperature variation maintained across a portion of the specimen-bearing surface contacting a biological specimen) can be equal to or less than about 5° temperature variation while a support surface of the support element contacting the back side surface of the slide has more than a 5° temperature variation.

A support surface of the support element can contact the back side surface of the slide and can be heated to produce a low heating zone at a central region of the support surface and a high heating zone at a region of the support surface surrounding the central region. Additionally or alternatively, the support surface can be heated to produce the high heating zone along a perimeter of a staining area along the specimen-bearing surface and a low heating zone at a central region of the staining area.

The slide can be conductively heated using thermal energy produced by a heating element of the conductive slide heating apparatus. The heating element includes at least two spaced apart elongate heating portions and two end heating portions extending between the elongate heating portions. The elongate heating portions and the end heating portions define a convection cooling pocket for cooling the support element.

In some embodiments, a system for heating a specimen-bearing slide including a slide platen including a support element, a conductive heater, and a controller. The support element has a support surface. The conductive heater is positioned to heat the support element. The controller is programmed to control the system to produce a non-uniform heating profile along the support element so as to transfer thermal energy to a slide to produce a substantially uniform temperature profile along a specimen-bearing area of a specimen-bearing surface of the slide when a back side of the slide contacts the support surface.

The conductive heater, in some embodiments, is configured to heat the support element to produce the non-uniform temperature heating profile across most of the support surface supporting the slide such that the substantially uniform temperature heating profile is produced along most of the specimen-bearing surface of the slide. The substantially uniform temperature profile has less than a 5° temperature variation across the specimen-bearing area of the slide. Additionally or alternatively, the conductive heater can be configured to produce a central low temperature heating zone along the support element and a peripheral high temperature heating zone along the support element. Additionally or alternatively, the conductive heater is positioned underneath the support element and defines an opening through which a convective flow is capable of passing to cool the support element.

The system for heating a specimen-bearing slide, in some embodiments, includes a convection cooling device coupled to the controller and configured to deliver a convective flow into the opening based on a signal from the controller. In certain embodiments, the convection cooling device includes at least one fan capable of producing the convective flow. In some embodiments, compressed air or motive air can be used.

The support element, in some embodiments, comprises stainless steel. In some embodiments, a portion of the support element between the support surface for carrying the slide and the conductive heater has a thermal conductivity equal to or less than about 20 W/m*K.

BRIEF DESCRIPTION OF THE DRAWINGS

Non-limiting and non-exhaustive embodiments are described with reference to the following drawings. The same reference numerals refer to like parts or acts throughout the various views, unless otherwise specified.

FIGS. 16A and 16B are side and top views of a narrowed band of liquid at an end of a gap between an opposable and a slide.

FIGS. 17A and 17B are side and top views of the spread band of liquid.

FIGS. 18A and 18B are side and top views of the band of liquid contacting a biological specimen.

FIGS. 19A and 19B are side and top views of the band of liquid between the opposable and a region of the slide adjacent to a label.

FIGS. 20A and 20B are side and top views of the narrowed band of liquid at an end of a gap adjacent to a label of the slide.

FIG. 28 is an isometric view of an opposable in accordance with an embodiment of the disclosed technology.

FIG. 29 is a top plan view of the opposable of FIG. 28.

FIG. 30 is a side elevational view of the opposable of FIG. 28.

FIG. 31 is a detailed view of a portion of the opposable of FIG. 30.

DETAILED DESCRIPTION OF TECHNOLOGY

Figure 1:
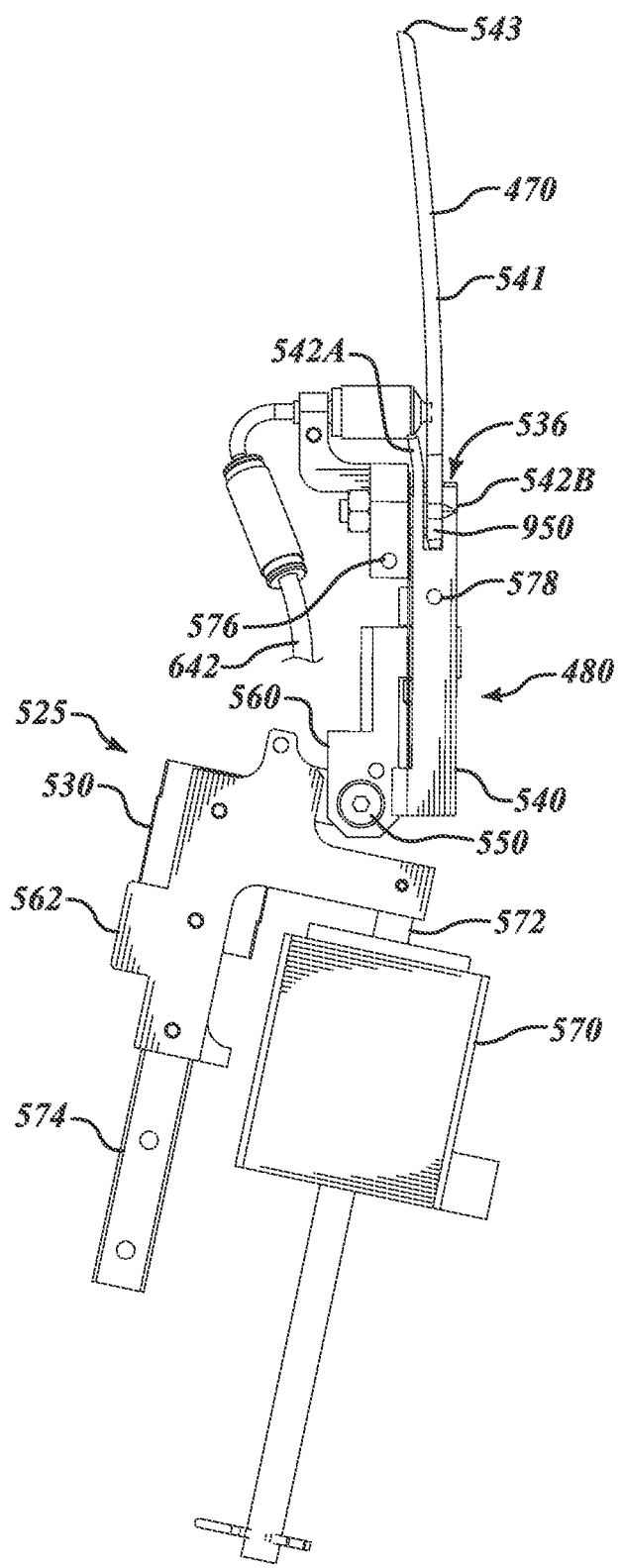
FIG. 1 is a side view of an opposable actuator holding an opposable in accordance with an embodiment of the disclosed technology.

FIG. 1 shows an opposable actuator 525 that includes an opposable receiver 480 and a drive mechanism 530. The opposable receiver 480 holds an opoposable 470 that can be used to manipulate and direct a series of liquids to a specimen. The opposable receiver 480 can include a clamp 536 and a main body 540. The clamp 536 includes a pair of jaws 542A, 542B that cooperate to hold a mounting end 950 of the opposable 470. The opposable 470 includes a main body 541 extending to a captivating end 543. The main body 541 is pivotally coupled to the drive mechanism 530 by a pivot 550. The drive mechanism 530 can include a linkage assembly 560 and a linear actuator assembly 562. The linkage assembly 560 includes the pivot 550, which allows rotation about one or more axes of rotation (e.g., two axes of rotation) and can include one or more roller ball bearings, pivots, hinges, or other features that provide desired motion. The linear actuator assembly 562 can include an energizable drive device 570 (e.g., a stepper motor, a drive motor, a solenoid, etc.), a moveable element 572 (e.g., a lead screw, a drive rod, etc.), and a rail assembly 574 (e.g., a carriage/rail assembly, a caged ball bearing linear rail assembly, etc.).

The opposable receiver 480 can be actuated by the linear actuator assembly 562 via the linkage assembly 560. The linear actuator assembly 562 can retract, and stationary cam(s) (e.g., cam 575 of FIG. 2) can engage, pins 576, 578 and drive the opposable receiver 480 to an open configuration. In some embodiments, including the illustrated embodiment of FIG. 1, the opposable receiver 480 in the open configuration can loosely hold the opposable 470. The opposable receiver 480 can be moved to a closed configuration by one or more biasing members (e.g., springs, pneumatic actuators, etc.). As the linear actuator assembly 562 extends, the pins 576, 578 can move upwardly and towards one another such that the biasing members close the opposable receiver 480.

The opposable actuator 525 can also include, without limitation, one or more sensors to detect the presence of the opposable 470, the position of the opposable 470, one or more characteristics of a processing liquid covered by the opposable 470, or the like. The sensors can include, without limitation, contact sensors, electromechanical sensors, optical sensors, or chemical sensors that can be coupled to or incorporated into the opposable receiver 480 or other suitable component. The number, positions, and configurations of the sensors can be selected to achieve the desired monitoring functionality.

Figure 2:
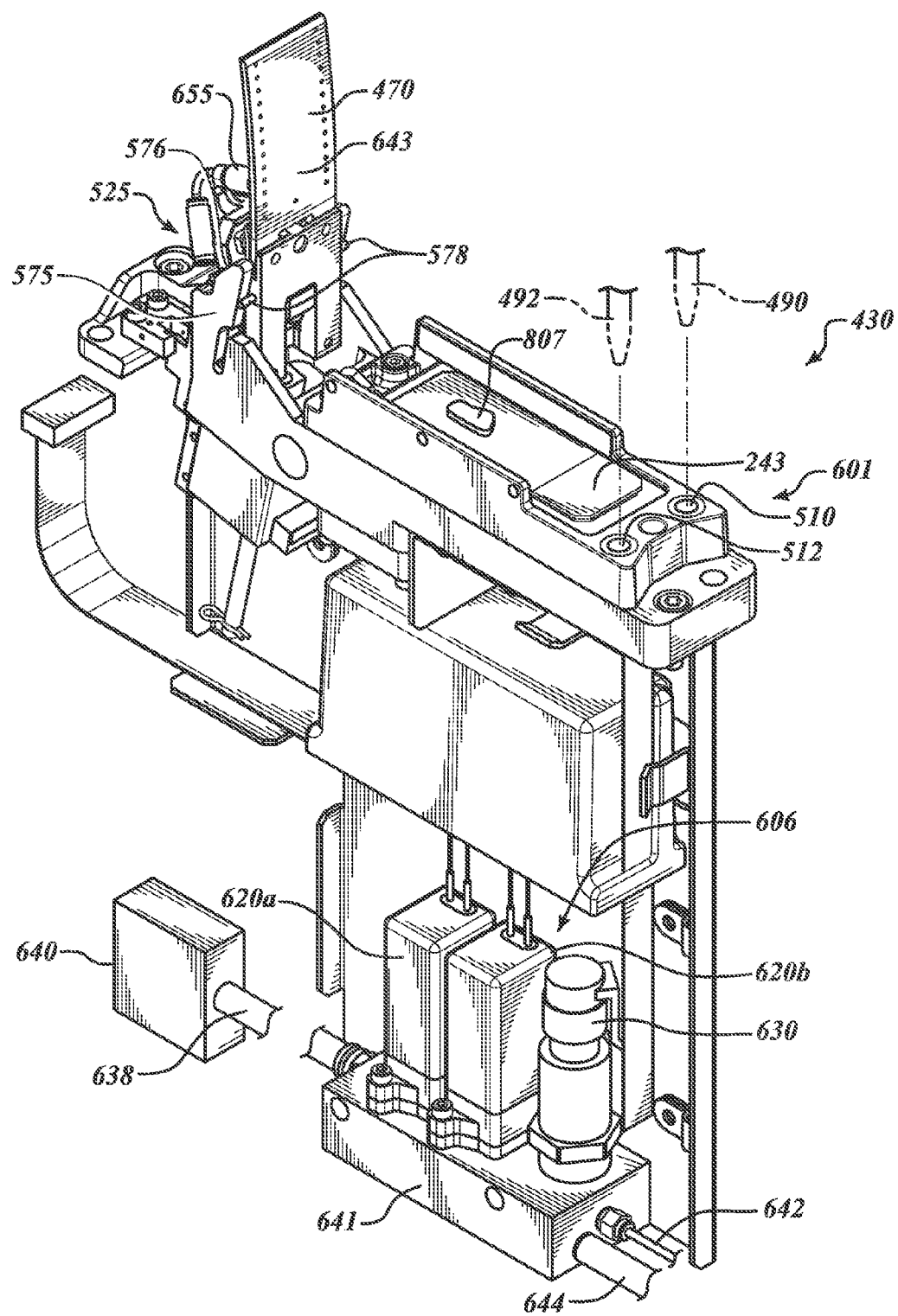
FIG. 2 is an isometric view of a specimen processing station ready to process a specimen on a slide in accordance with an embodiment of the disclosed technology.

FIG. 2 is an isometric view of a wetting module 430 holding a slide 243 in accordance with an embodiment of the present technology. The wetting module 430 includes the opposable actuator 525, a slide holder platen 601, and a manifold assembly 606. The opposable actuator 525 in a rolling state of operation can be extended or retracted to roll the opposable 470 back and forth along the slide 243. The motion of the rotary joints of the linkage assembly 560 (FIG. 1), gravity, and/or liquid capillary forces can help maintain the desired motion of the opposable 470. In some embodiments, the opposable actuator 525 can continuously or periodically roll (e.g., longitudinally roll, laterally roll, or both) the opposable 470 to agitate the volume of liquid, move (e.g., translate, spread, narrow, etc.) a band of liquid (e.g., a meniscus layer of liquid), control evaporation (e.g., to moderate evaporation), and/or otherwise manage the processing liquid.

The manifold assembly 606 includes a pair of sensors 620a, 620b (collectively "620") and a one or more valves 630. The sensors 620 can detect the pressures of working fluids and can send one or more signals indicative of detected pressures. A fluid line 638 can fluidically couple a pressurization source 640 to a manifold 641. Fluid lines 642, 644 fluidically couple the manifold 641 to a liquid removal device 655 and the slide holder platen 601. The liquid removal device 655 can remove liquid between the opposable 470 and the slide 243 via a waste port 643. The line 644 can be used to draw a vacuum to hold the slide 243 on the slide holder platen 601.

Figure 3A:
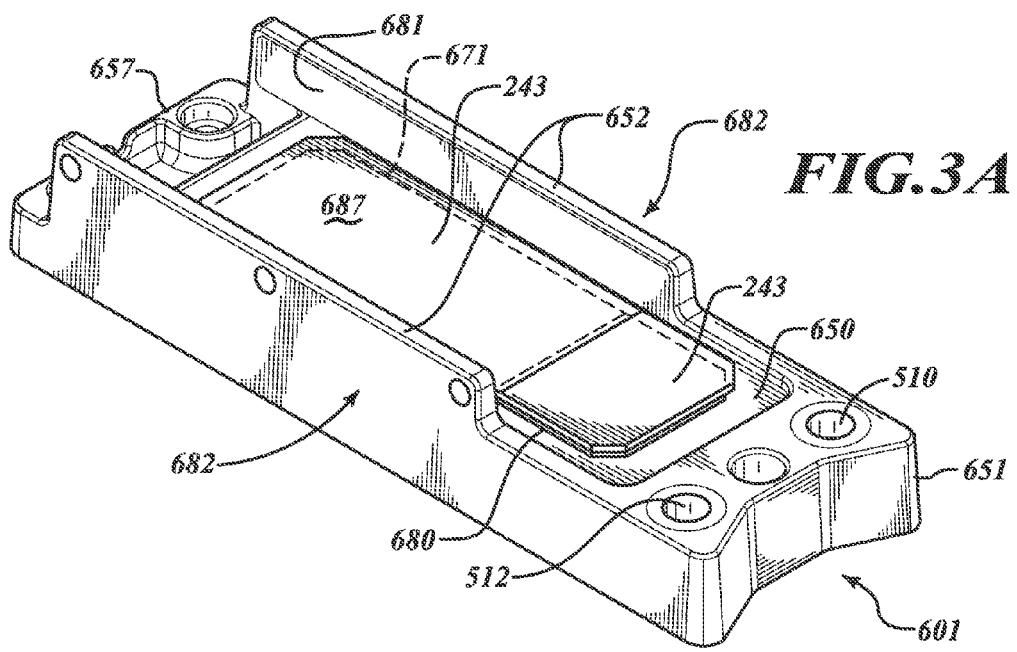
FIG. 3A is a front, top, left side isometric view of a slide holder platen holding a slide in accordance with an embodiment of the disclosed technology.
Figure 3B:
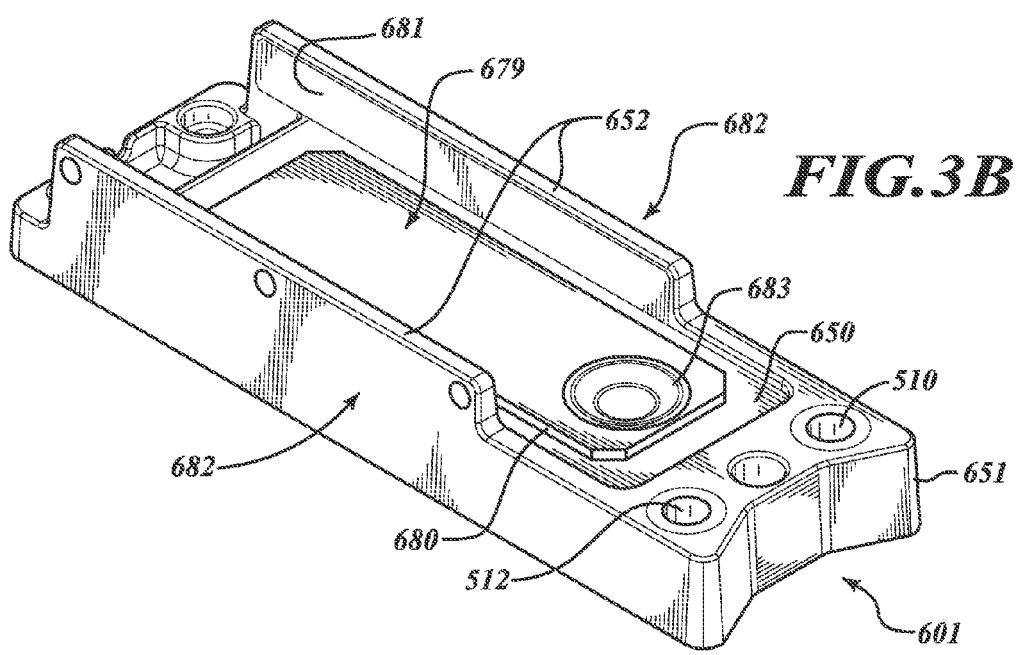
FIG. 3B is a front, top, left side isometric view of the slide holder platen of FIG. 3A ready to hold a slide in accordance with an embodiment of the disclosed technology.

FIGS. 3A and 3B are isometric views of the slide holder platen 601 in accordance with an embodiment of the present technology. The slide holder platen 601 of FIG. 3A supports the slide 243. The slide holder platen 601 of FIG. 3B is empty. The slide holder platen 601 can include a support element 650 and a mounting base 651. The support element 650 includes a raised slide receiving region 680 having a contact or contact surface 679 (FIG. 3B). A port 683 (FIG. 3B) is positioned to draw a vacuum to hold the slide 243 against the contact surface 679. The port 683 can be a suction cup or other feature configured to facilitate drawing a strong vacuum between the slide 243 against the contact surface 679.

The support element 650 includes inner walls 681 positioned in outer walls 652 of the mounting base 651. The inner and outer walls 681, 652 form heatable sidewalls 682. In some embodiments, the sidewalls 682 can be positioned on both sides of the contact surface 679 and can output heat energy to the surrounding air to control the temperature of the slide 243, processing fluid, and/or specimen(s). In some embodiments, the sidewalls 682 can also be positioned to laterally surround the entire slide 243. The mounting base 651 can be made of an insulating material (e.g., plastic, rubber, polymers, or the like) that can insulate the support element 650 from other components. In some embodiments, the mounting base 651 is made of a material with a thermal conductivity that is substantially less than the thermal conductivity of the material of the support element 650. The mounting base 651 can surround and protect the support element 650 and includes a coupling region 657 to which the opposable actuator 525 can be coupled.

The support element 650 can be an uncoated element comprising one or more low heat transfer material(s) with a low thermal conductivity. Low heat transfer materials can include, without limitation, steel, stainless steel, or other materials with a thermal conductivity in a range of about 10 W/(m*K) at 25° C. to about 25 W/(m*K) at 25° C. In one embodiment, the low heat transfer material comprises stainless steel with a thermal conductivity of 16 W/(m*K) at 25° C. In some embodiments, the support element 650 comprises mostly stainless steel by weight. In certain embodiments, at least most of the material of the support element 650 directly between a heating element 653 (FIG. 4) and the slide 243 comprises stainless steel by weight. The stainless steel support element 650 can be corrosion-resistant to the liquids used to process the specimens to provide a relatively long working life. In some embodiments, support element 650 comprises antimony (k=18.5 W/(m*K) at 25° C.) or chrome nickel steel (e.g., 18% Cr and 8% Ni by weight and with a thermal conductivity of about 16.3 W/(m*K) at 25° C.). In other embodiments, the support element 650 can comprise lead with a thermal conductivity of about 35 W/(m*K) at 25° C.) or other metal with a similar thermal conductivity. In some embodiments, the support element 650 can be made of a material with thermal conductivity less than copper or brass. The mounting base 651 can be made of an insulating material with a thermal conductivity that is less than the thermal conductivity of the support element 650. As such, the mounting base 651 can thermally insulate the support element 650.

Figure 4:
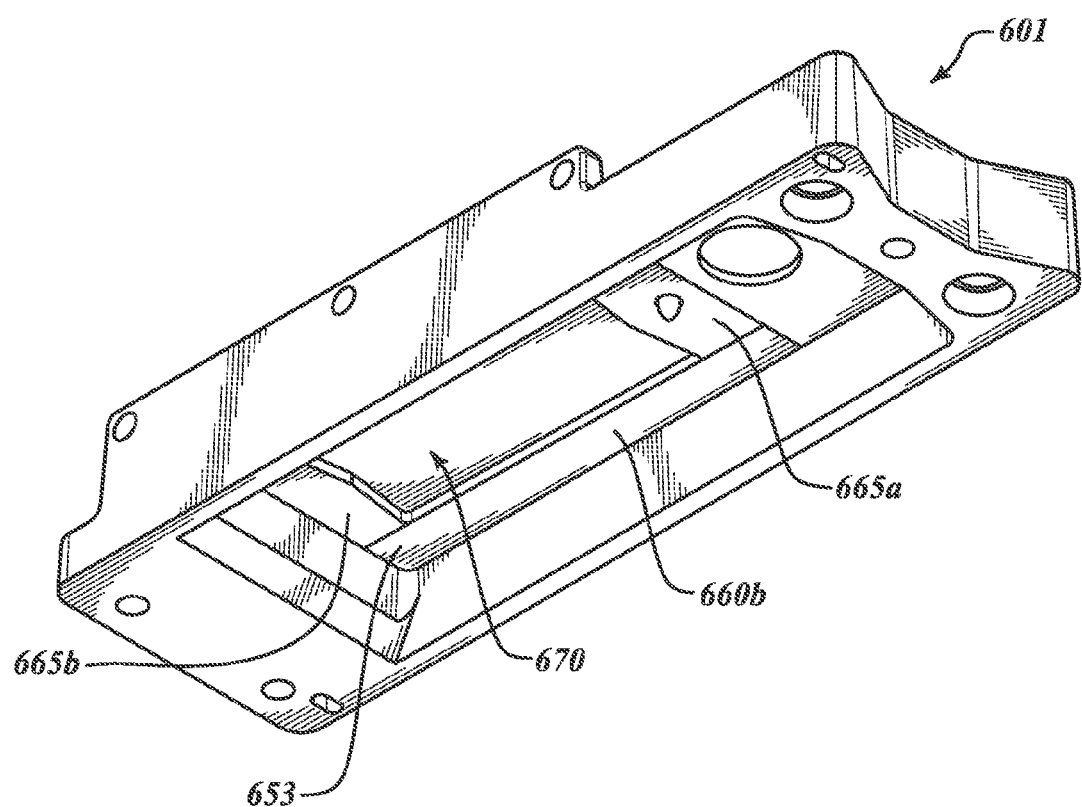
FIG. 4 is a front, bottom, left side isometric view of the slide holder platen of FIG. 3A.
Figure 5:
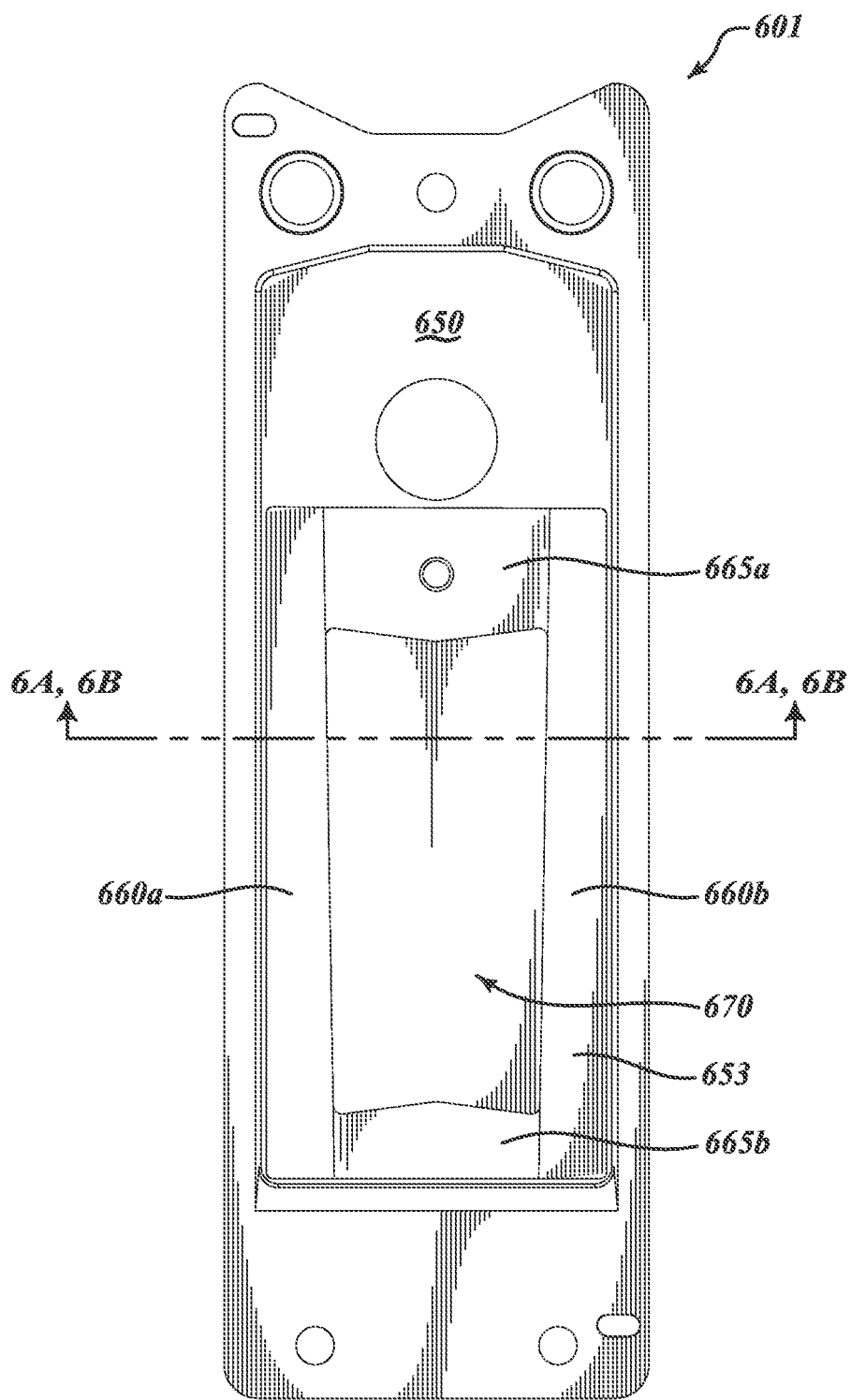
FIG. 5 is a bottom view of the slide holder platen of FIG. 3A.

FIG. 4 is a front, bottom, left side view of the slide holder platen 601. FIG. 5 is a bottom view of the slide holder platen 601. The slide holder platen 601 can include the heating element 653, which can convert electrical energy to thermal energy and can include, without limitation, one or more traces, leads, resistive elements (e.g., active elements that produce thermal energy), fuses, or the like. In some embodiments, the heating element 653 can be a resistive heater. Other types of heaters can also be used, if needed or desired. In some embodiments, the heating element 653 can output thermal energy to the support element 650 to achieve a desired heat transfer pattern. Heat can be transferred non-uniformly to the slide 243 via the support element 650 to compensate for evaporative heat losses. Non-uniform heat transfer along the contact surface 679 may produce a non-uniform temperature profile along the contact surface 679. A generally uniform temperature profile can be produced across a processing zone 671 (FIG. 3A) of slide 243. The processing zone 671 can be a staining region, a mounting region, or area of an upper or specimen-bearing surface 687 (FIG. 3A) of the slide 243 suitable for carrying one or more specimen(s).

The heating element 653 of FIG. 5 can include two elongate slide heating portions 660a, 660b (collectively 660) and two end heating portions 665a, 665b (collectively "665"). The elongate portions 660 deliver thermal energy to the longitudinally extending edge portions of the slide 243. The end heating portions 665 deliver thermal energy to the ends of the processing zone 671. The elongate portions 660 and the end heating portions 665 can be coupled together to form a multi-piece heating element 653. The elongate portions 660 and the end heating portions 665 can be made of materials with the same conductivity or different thermal conductivities. Each portion 660, 665 can be independently operated to output different amounts of thermal energy. In other embodiments, the heating element 653 can have a one-piece construction with a uniform thickness or a variable thickness. The one-piece heating element 653 can be made of one material.

The elongate portions 660 and end heating portions 665 together define a convection cooling feature in the form of a pocket 670. The pocket 670 can help isolate heat in the support element 650 to help keep thermal energy at the location it is applied and can also help reduce or limit the thermal mass of the slide holder platen 601. The pocket 670 can be an opening with a substantially rectangular shape, as shown in FIG. 5. However, the pocket 670 can have other shapes based on the desired heat distribution along the contact surface 679 of the support element 650.

Figure 6A:
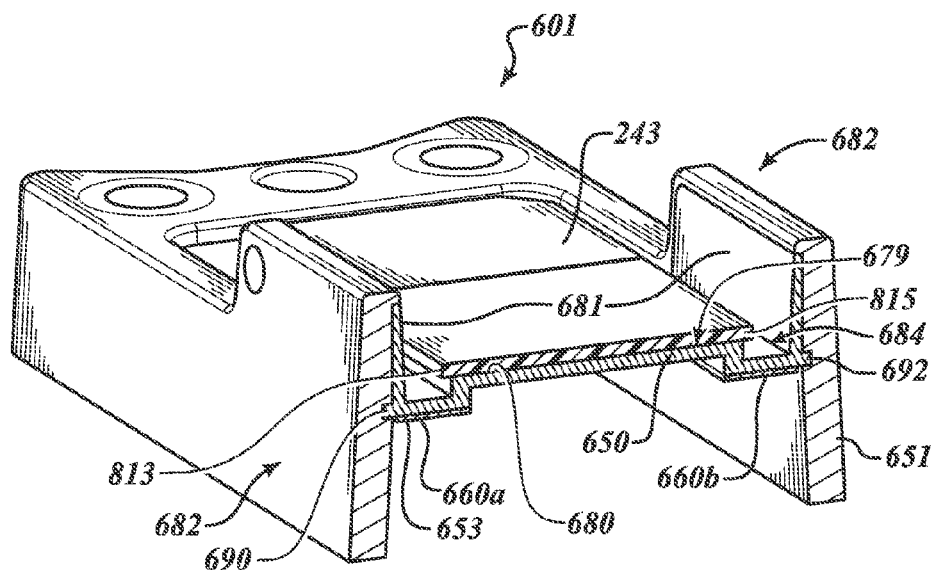
FIG. 6A is a cross-sectional isometric view of the slide holder platen taken along a line 6A-6A of FIG. 5.

FIG. 6A is a cross-sectional isometric view of the slide holder platen 601. The support element 650 includes the receiving region 680, sidewalls 682, and a channel 684. The receiving region 680 keeps the slide 243 spaced apart from fluids that can collect in the channel 684 during operation. The channel 684 can collect liquid that falls from edges 813, 815 of the slide 243. In some embodiments, the slide 243 can extend outwardly from the receiving region 680 a sufficient distance (e.g., 0.5 mm, 0.75 mm, 1 mm, 2 mm, 4 mm, or 6 mm) to prevent liquid from wicking between the slide 243 and the contact surface 679.

The slide holder platen 601 can be made in a multi-step manufacturing process. The support element 650 can be formed by a machining process, stamping process, or the like. The support element 650 can be over-molded to form the mounting base 651, which can be made of an insulating material molded using an injection molding process, compressing molding processes, or other suitable manufacturing processes. Exemplary non-limiting insulating materials include, without limitation, plastics, polymers, ceramics, or the like. The support element 650 and mounting base 651 can remain securely coupled together to inhibit or prevent liquids from traveling between the support element 650 and mounting base 651. For example, the interface between the supporting element 650 and the mounting base 651 can form a fluid-tight seal with or without utilizing any sealants. However, sealants, adhesives, and/or fasteners can be used to securely couple the support element 650 to the mounting base 651. The illustrated support element 650 includes locking features 690, 692 to help minimize, limit, or substantially prevent movement of the support element 650 relative to the mounting base 651.

Figure 6B:
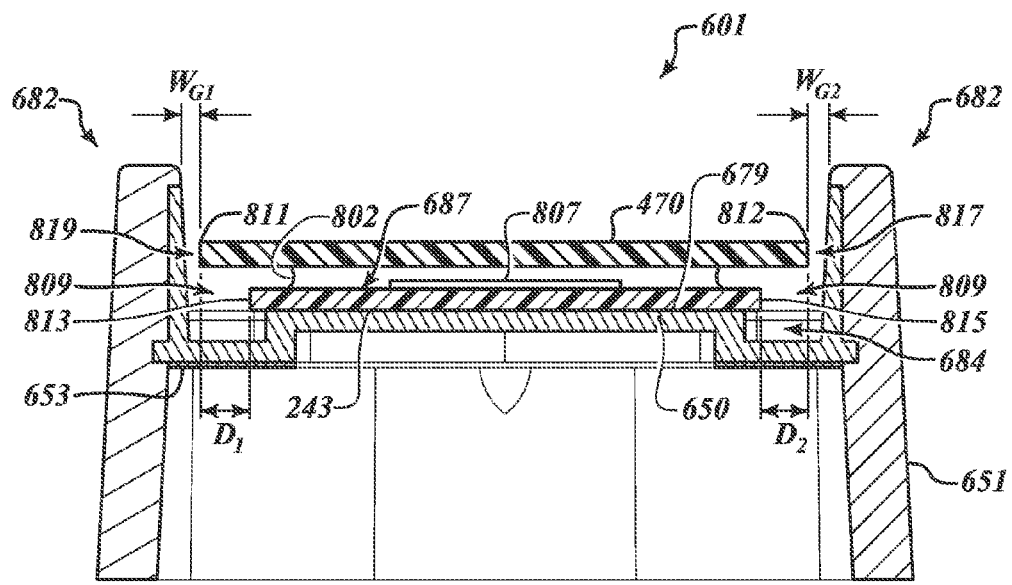
FIG. 6B is a cross-sectional view of the slide holder platen taken along a line 6B-6B of FIG. 5.

FIG. 6B is a cross-sectional view of the slide holder platen 601. The opposable 470 engages a liquid 802 which engages a specimen 807. The sidewalls 682 can extend vertically above the slide 243. The distance that the sidewalls 682 extend vertically past the slide 243 can be selected to manage (e.g., limit, minimize, substantially prevent, etc.) air currents that can cause heat losses via convection (e.g., convection via the surrounding air), evaporation, or the like. For example, the slide holder platen 601 and opposable 470 can moderate evaporation by keeping the evaporation rate of the liquid 802 at or below about 7 microliters per minute, 5 microliters per minute, 3 microliters per minute or other maximum evaporation rates. In some embodiments, the slide holder platen 601 and opposable 470 can keep the evaporation rate of the liquid 802 within a range of about 7 microliters per minute to about 1 microliters per minute. Such embodiments can moderate evaporative losses. The sidewalls 682 and the opposable 470 can also cooperate to help thermally isolate the fluid 802 from the surrounding environment.

A side portion 811 of the opposable 470 extends outwardly past the edge 813 of the slide 243 such that the side portion 811 is closer to the sidewall 682 than the edge 813 of the slide 243. A width $W_{G1}$ of a gap 819 can be smaller than a distance $D_1$ from the side portion 811 to the slide edge 813. A side portion 812 of the opposable 470 extends outwardly past the edge 815. A width $W_{G2}$ of a gap 817 can be smaller than a distance $D_2$ from the side portion 812 to the slide edge 815. In some embodiments, width $W_{G1}$ can be equal to or less than about 10%, 25%, or 50% of a distance between the left sidewall 682 and the edge 813. Similarly, width $W_{G2}$ can be equal to or less than about 10%, 25%, or 50% of a distance between the right sidewall 682 and the slide edge 815. The widths $W_{G1}$, $W_{G2}$ can be sufficiently small to inhibit or limit evaporative losses while allowing slight side-to-side movement of the opposable 470 to facilitate convenient handling. In some embodiments, the widths $W_{G1}$, $W_{G2}$ are equal to or less than about 1 mm, 2 mm, 4 mm, or other suitable widths.

Figure 7:
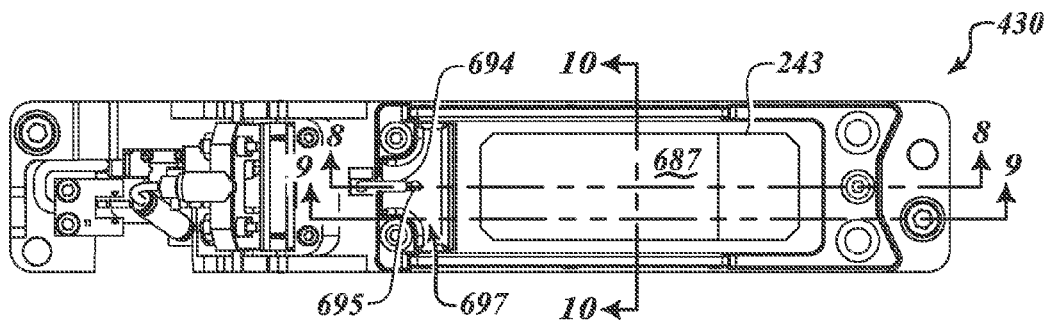
FIG. 7 is a top plan view of a specimen processing station holding a specimen-bearing slide in accordance with an embodiment of the disclosed technology.
Figure 8:
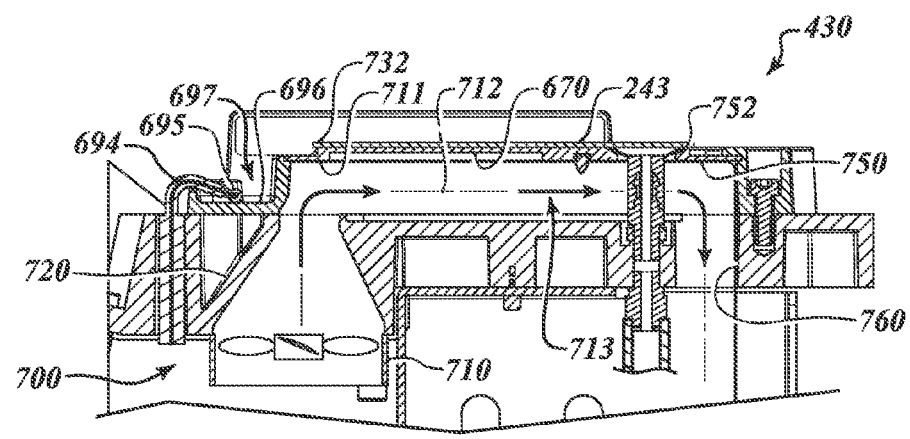
FIG. 8 is a cross-sectional view of a portion of the specimen processing station taken along a line 8-8 of FIG. 7.
Figure 9:
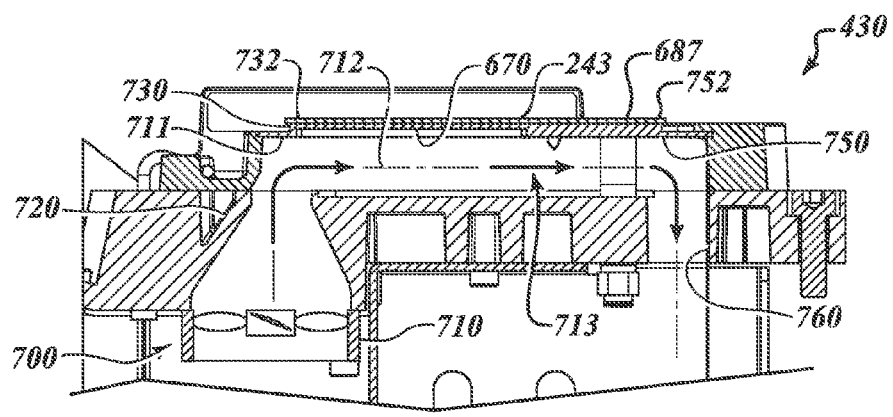
FIG. 9 is a cross-sectional view of a portion of the specimen processing station taken along a line 9-9 of FIG. 7.

FIG. 7 is a top plan view of the wetting module 430. FIG. 8 is a cross-sectional view of a portion of the wetting module 430 taken along a line 8-8 of FIG. 7. FIG. 9 is a cross-sectional view of a portion of the wetting module 430 taken along a line 9-9 of FIG. 7. Referring to FIGS. 7 and 8, a sensor 694 is positioned to detect liquid in a reservoir 697. The sensor 694 can include a thermistor element 695 positioned near a bottom 696 of the reservoir 697. When a sufficient volume of liquid is collected to contact the thermistor element 695, the sensor 694 sends a signal to another component, such as a controller. The detection of a threshold volume of liquid in the reservoir 697 can indicate a failure in the wetting module 430. Upon detection of a failure, the wetting module 430 can be disabled until the wetting module 430 can be, for example, inspected, cleaned, or otherwise maintained.

Referring to FIGS. 8 and 9, the wetting module 430 includes a convection system 700 that includes a flow generator 710, a duct 711, and a flow path 712 (illustrated in phantom line) defined by a passageway 713 of the duct 711. The flow generator 710 can include, without limitation, one or more fans, blowers, or other suitable components capable of generating a sufficient flow of a convection fluid (e.g., air, a refrigerant, etc.) along the flow path 712 to cool the back side of the support element 650, the slide 243, and/or items (e.g., specimens, reagents, or the like) carried on the slide 243.

The flow generator 710 can deliver the convection fluid towards an end 730 of the support element 650 located under a first end 732 of the slide 243. The convection fluid can travel vertically through a tapered section 720 that can accelerate the flow of convection fluid. The accelerated flow is directed horizontally and flows under the slide platen 601. The convection fluid can directly contact the support element 650 to facilitate and expedite cooling of the slide 243. For example, the convection fluid can flow into and along the pocket 670 to absorb thermal energy from the support element 650. The support element 650 absorbs thermal energy from the slide 243 to cool the upper surface 687 and to ultimately cool a liquid, specimen(s), or any other items or substances on the upper surface 687. The warmed fluid flows past the pocket 670 and proceeds under an end 750 of the support element 650 positioned underneath a label end 752 of the slide 243. The air flows downwardly through an outlet 760 to the surrounding environment.

The convection system 700 can be used to rapidly cool the slide 243. For example, the convection system 700 can help cool the liquid and/or specimen at a rate equal to or greater than about 2.5° C./sec. In one embodiment, the temperature of a specimen can be at about 95° C. and can be cooled to a temperature equal to or less than about 30° C. in about four minutes or less. Other cooling rates can be achieved by increasing or decreasing the flow rate of the convection fluid, temperature of the convection fluid, or the like. During a heating cycle, the convention system 700 can be OFF, if desired.

Figure 10:
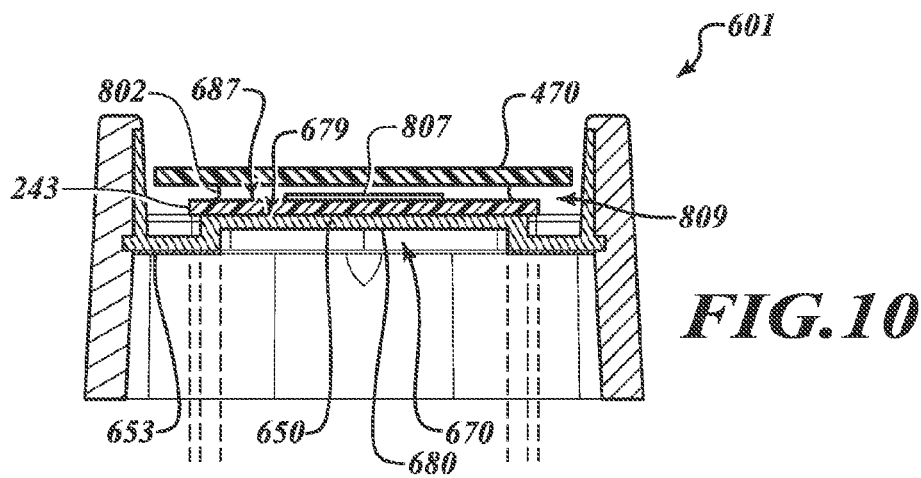
FIG. 10 is a cross-sectional view of a slide holder platen taken along a line 10-10 of FIG. 7.

FIG. 10 is a cross-sectional view of a portion of the slide holder platen 601 taken along a line 10-10 of FIG. 7. The temperature of the liquid 802 can be maintained within a target temperature range selected based on the characteristics of the liquid 802, characteristics of a specimen (e.g., a thickness of the specimen, composition of the specimen, etc.), and the process to be performed. Because the regions of the liquid 802 nearest the edges of the slide 243 evaporate more than the central region of the liquid 802, the periphery of the slide 243 and the periphery of the liquid 802 tend to be at a lower temperature without compensation. The evaporative heat losses for high temperature processes (e.g., antigen retrieval) may be greater than the evaporative losses for low temperature processes (e.g., rinsing). Because significant temperature variations along the specimen 807 and/or the liquid 802 can lead to variations in processing, the wetting module 430 can maintain a desired temperature profile of the slide 243 by compensating for evaporative heat losses, including evaporative heat losses in high temperature and low temperature processes. The wetting module 430 can produce a substantially uniform temperature profile along the surface 687 to substantially uniformly heat the band of liquid 802 and/or the specimen 807. The uniform temperature profile can be maintained independently of changes in the surrounding environment to consistently process the entire specimen 807.

Figure 10A:
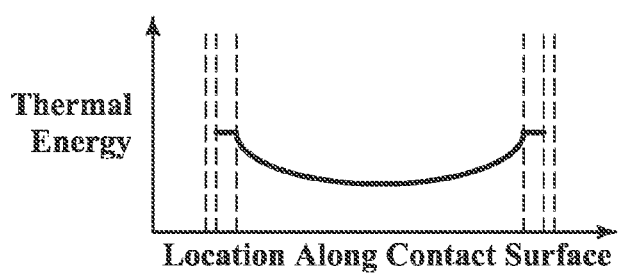
FIG. 10A is a plot of location along a contact surface of a slide support versus thermal energy conducted to a slide in accordance with an embodiment of the disclosed technology.
Figure 10B:
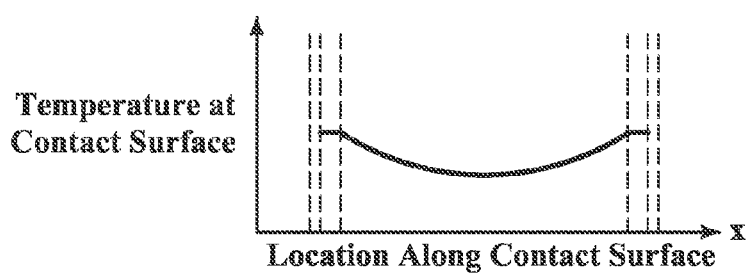
FIG. 10B is a plot of location along the contact surface of the slide support versus temperature of the contact surface in accordance with an embodiment of the disclosed technology
Figure 10C:
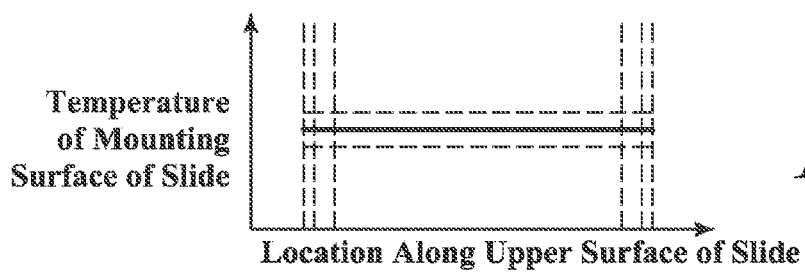
FIG. 10C is a plot of location along an upper surface of a slide versus temperature of the upper surface of the slide in accordance with an embodiment of the disclosed technology.

FIG. 10A is a plot of the location along the width of the receiving region 680 versus thermal energy conducted to the slide 243. FIG. 10B is a plot of the location along the width of the receiving region 680 versus a temperature of the contact surface 679 of the support element 650. FIG. 10C is a plot of a location along the upper surface 687 of the slide 243. A comparison of FIGS. 10B and 10C shows that the temperature profile along the contact surface 679 of the support element 650 is different from the temperature profile along the upper surface 687 of the slide 243.

Referring to FIG. 10A, the heating element 653 can non-uniformly transfer heat energy via conduction to the slide 243. The heat remains concentrated at the perimeter of the staining region where evaporative heat losses are relatively high. Because no heat energy is directly transferred via conduction to the portion of the support element 650 above the pocket 670, a non-uniform temperature profile is produced along the contact surface 679 of the support element 650 and can compensate for non-uniform heat losses associated with evaporation of the liquid 802. The compensation can produce a substantially uniform temperature profile along the upper slide surface 687. As shown in FIG. 10C, a temperature along the upper slide surface 687 can be kept within a target temperature range (represented by two horizontal dashed lines). In an embodiment for antigen retrieval, the substantially uniform temperature profile can have a temperature variation that is equal to or less than 5% of the desired temperature and can be across most of the upper slide surface 687. The upper slide surface 687 can be kept at, for example, an average temperature or target temperature of about 95° C. and within a range of about 90.25° C. and about 99.75° C. In some embodiments, the heater element 653 produces less than about a 4% temperature variation across most of the upper slide surface 687. In other embodiments, there can be less than 5% temperature variation across most of the upper slide surface 687. The upper slide surface 687 can be kept at, for example, an average temperature of about 95° C. and within a range of about 92.63° C. and about 97.38° C. In some embodiments, an allowable temperature variation can be inputted by a user.

Figure 11:
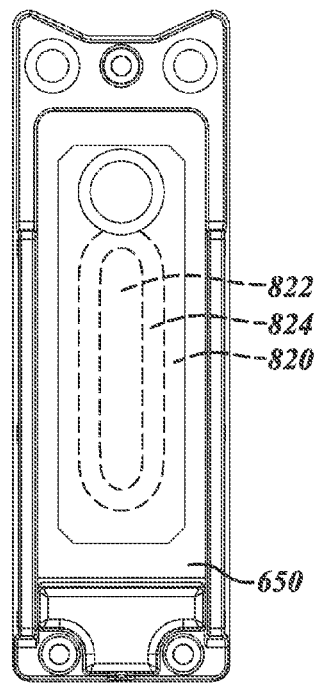
FIG. 11 is a top plan view of heating zones produced on a slide support surface of the support element in accordance with an embodiment of the disclosed technology.

FIG. 11 is a top view of heating zones in accordance with an embodiment of the present technology. A high heating zone 820 surrounds an intermediate heating zone 824. The intermediate heating zone 824 surrounds a low heating zone 822. Heat from the heating element 653 primarily travels upwardly to define the high heating zone 820. The high heating zone 820 can be located underneath a perimeter of a staining area of the slide 243. The low heating zone 822 can generally correspond to the pocket 670 and the central processing area (e.g., a staining area) where one or more specimens are typically positioned. The temperature of the heating zones 820, 822, 824 can be generally inversely proportional to the rates of evaporation along the slide directly above that heating zone. For example, the low heating zone 822 can be positioned generally below the middle of the band of liquid 802 in which there is substantially no evaporative losses. The high heating zone 820 is positioned generally below the periphery of the band of liquid 802 that experiences relatively high evaporative losses.

Figure 12:
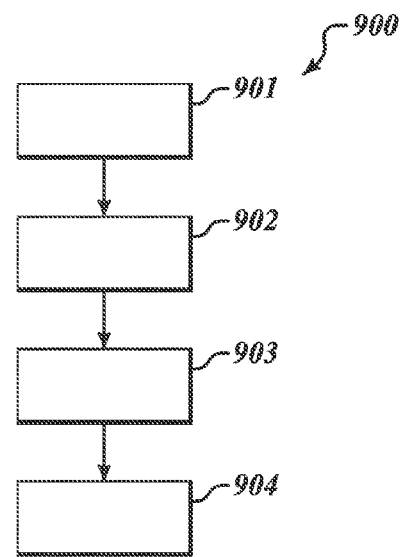
FIG. 12 is a flow chart illustrating a method for heating a slide in accordance with an embodiment of the disclosed technology.

FIG. 12 is a flow chart illustrating a method 900 for heating the slide in accordance with an embodiment of the present technology. At 901, the specimen-bearing slide 243 (FIG. 3A) can be positioned on the contact surface 679 of the support element 650 (FIG. 3B). The slide 243 can be preheated by the slide holder platen 601. A liquid can be delivered onto the heated slide 243. Alternatively, the slide holder platen 601 can heat the slide 243 after delivering the liquid.

At 902, the opposable 470 is used to manipulate the liquid and can mitigate and control evaporation, which in turn can affect temperature, concentration, and capillary volume. In some embodiments, the liquid is allowed to evaporate, resulting in heat losses and, in some embodiments, changes in concentration of the liquid 802. A dispenser can deliver supplemental liquid at desired times to keep the volume of the liquid in a desired range, maintain a desired concentration of the liquid, or the like. If the current volume of the liquid is lower than the target equilibrium volume, the controller can instruct the dispenser to deliver liquid until the current volume of the liquid reaches the equilibrium volume. If the current volume of the liquid is higher than the target equilibrium volume, the controller can instruct the dispenser to stop delivering liquid until the current volume of the liquid reaches the equilibrium volume. Once the liquid reaches the target equilibrium volume, the controller can instruct the dispenser to provide the supplemental fluid to the liquid at a desired rate (e.g., a fixed rate or a variable rate), so as to maintain the liquid at the equilibrium volume. The delivery rate can be selected based on the evaporation rate of the liquid.

At 903, the contact surface 679 can have a non-uniform temperature profile such that the upper surface 687 of the slide 243 has a temperature profile that is more uniform than the non-uniform profile of the contact surface 679. Substantially the entire mounting area of the slide 243 can have a substantially uniform profile. This ensures that any portion of a specimen contacting the mounting surface is maintained at a generally uniform temperature for consistent processing. Even if specimens move slightly along the mounting surface, the specimens can be consistently processed.

At 904, heat losses associated with evaporation of the liquid 802 can be compensated for by producing the non-uniform temperature profile along the contact surface 679. The support element 650 and the heating sidewalls 682 can be used to control the temperature of the slide 243.

Fluid manipulated repeatedly across the staining surface results in fluid mixing between different regions within the body of fluid in contact with the slide surface in the sense of both mass as well as thermal energy mixing. Temperature uniformity control across the surface of the slide, therefore, is influenced by the interaction of 1) the conducting heating element under the slide, 2) thermal mixing resulting from fluid manipulation, and 3) evaporative heat loss with respect to the ambient environment. Fluid manipulation is controlled by such factors as manipulation speed and distance with respect to specified volumes. The thermal profile of the conducting element under the slide therefore must be designed appropriately for optimal on-slide temperature uniformity with respect to fluid manipulation factors.

Figure 13:
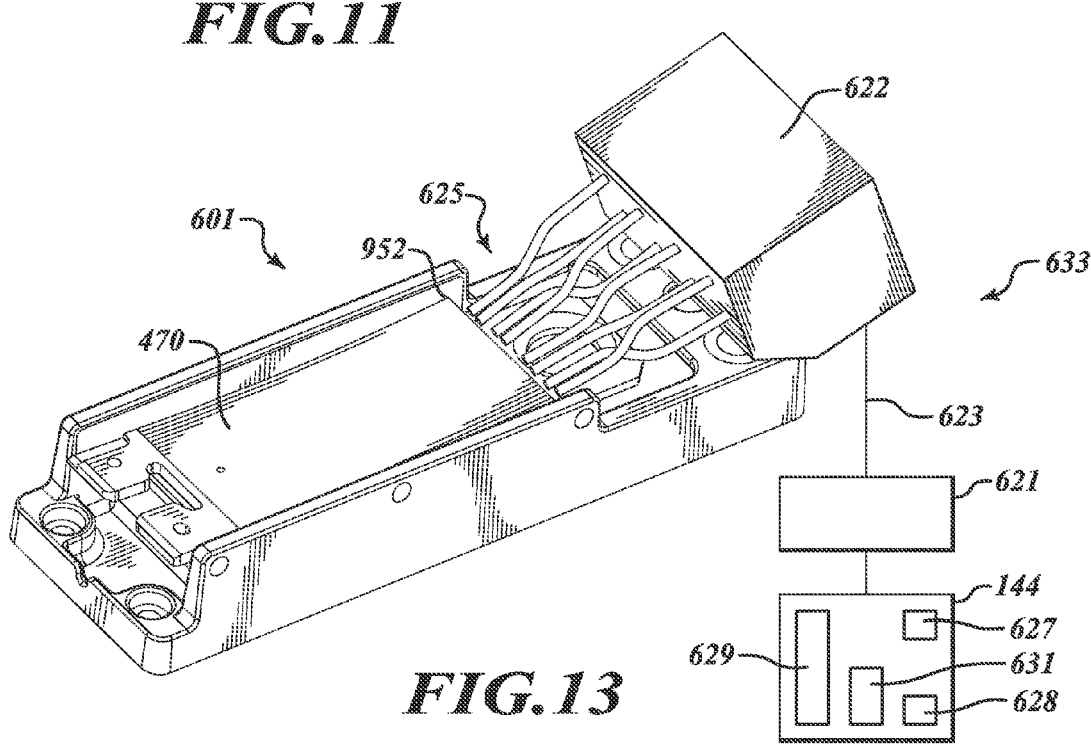
FIG. 13 illustrates a slide holder platen and a dispenser assembly in accordance with an embodiment of the disclosed technology.

FIG. 13 shows the slide holder platen 601, a dispenser assembly 633, and a controller 144 of an evaporation moderated specimen process station. The dispenser assembly 633 includes a fluid source 621 fluidically coupled to a dispenser 622 via a fluid line 623. The fluid source 621 can include, without limitation, one or more containers (e.g., a container taken from a parking or holding station, a container taken from a parking or holding station, etc.), reservoirs, or other suitable fluid sources (e.g., a bulk reagent reservoir) and can include one more valves, pumps, or the like. The dispenser 622 can output liquid via an array of conduits 625. In some embodiments, including the illustrated embodiment of FIG. 13, the dispenser 622 includes eight conduits 625, but any number of conduits can be used. Additionally, the dispenser assembly 633 can include more than one dispenser depending on the design of the slide holder platen 601. Additionally or alternatively, dispensers can deliver liquid onto the slides and can be fluidly coupled to the fluid source 621 or another fluid source. The opposable 470 can be positioned to allow one or both of the dispensers 160, 162 to deliver a liquid onto the slide. In some embodiments, the dispenser 622 delivers a bulk liquid from the containers at the parking station 142 and the dispensers 160, 162 deliver liquid from containers at the parking station 140.

The controller 144 is capable of controlling an array of specimen processing stations to keep a volume of a processing liquid within an equilibrium volume range. If the volume of the liquid is above the equilibrium volume range, the liquid can evaporate at a relatively high rate and may significantly change the concentration of the liquid. If the volume of the liquid is below the equilibrium volume range, there may be an insufficient volume of liquid to adequately process the specimen. Additionally, an insufficient volume of liquid can result in an undesirably low amount of liquid agitation during processing. The equilibrium volume range can be selected based on the composition of the liquid, desired processing temperature, or desired agitation of the liquid 802. An equilibrium volume of the liquid 802 can correspond to a fluid volume (at a certain temperature or range of temperatures) that provides full coverage of the specimen while keeping evaporative losses below a target level. The dispenser 622 can function as a replenishment device that periodically supplements the liquid at a fixed rate (e.g., a rate based on the evaporation rate) to keep the volume of the liquid within the equilibrium volume range, replenish depleted reagent, or the like.

With the target processing temperature or target processing temperature range and a total evaporation rate, the controller 144 can determine a target range of equilibrium volumes. In some embodiments, the controller 144 can receive the total evaporation rate information from a memory 629 and/or an input device 628. The input device 628 can include a data server or other similar device that can provide information from a database upon request or periodically. The total evaporation rate information can be obtained from an empirical study and stored in the database. In other embodiments, the input device 628 can be a reader that obtains information (e.g., a target processing temperature, a target processing temperature range, replenishing rate, etc.) from a label of a slide.

The controller 144 can receive information (e.g., look-up tables, temperature set points, duty cycles, power settings, environmental information such as ambient temperatures and/or humidity, processing protocols, etc.) from the memory 629. The input device 628 can be a manual input device (e.g., a keyboard, a touch screen, or the like) or an automated input device (e.g., a computer, a data storage device, servers, network, etc.) that can provide information automatically upon request from the controller 144. The memory 629 can store different instructions for different processes. One stored sequence of program instructions can be used to contact the specimen 807 with a wash and another sequence of program instructions can be used to apply a reagent (e.g., a stain) to the specimen. The controller 144 can include a programmable processor 631 that executes the sequence of program instructions in order to sequentially process the specimen with the wash and reagent. The slide holder platen 601 can heat the slide to a first target temperature when executing the first sequence of program instructions and can cool the slide to a second target temperature when executing the second sequence of program instructions. Any number of sequences of program instructions can be executed to perform different stages of a protocol.

The controller 144 can also be programmed to control the wetting module 430 such that the dispenser 622 delivers the supplemental liquid onto the slide. The rate of fluid delivery can be based on, for example, processing information (e.g., protocol, agitation information, processing time(s), etc.), total evaporation rate information (e.g., evaporation rates under certain conditions, the actual evaporation rate for a certain type of liquid, etc.), or the like. The current volume of the liquid can be determined based on an initial volume of liquid on the slide and stored evaporation rate(s). The stored evaporation rates can be input into the system 100 or determined by the system 100. The controller 144 can calculate the equilibrium volume in advance (e.g., a pilot run), and the system 100 can use the determined equilibrium volume as the initial volume for the same kind of liquids. Then the controller 144 can instruct the dispenser 622 to provide the supplemental liquid at a rate (e.g., a rate determined by the pilot run). The rolling direction, the rolling speed, and the rolling frequency can be adjusted depending on the type of liquids. The rolling speed can have a direct impact on the total evaporation rate. A faster rolling speed can lead to higher evaporation rates. When collecting empirical total evaporation volume information to generate protocols, this can be a factor that is considered.

A power source 627 of the controller 144 can be electrically coupled to a heating element (e.g., heating element 653 of FIGS. 6A and 6B). The power source 627 can be one or more batteries, fuel cells, or the like. The power source 627 can also deliver electrical energy to other components of the system. In other embodiments, the power source 627 can be an AC power supply.

Figure 14:
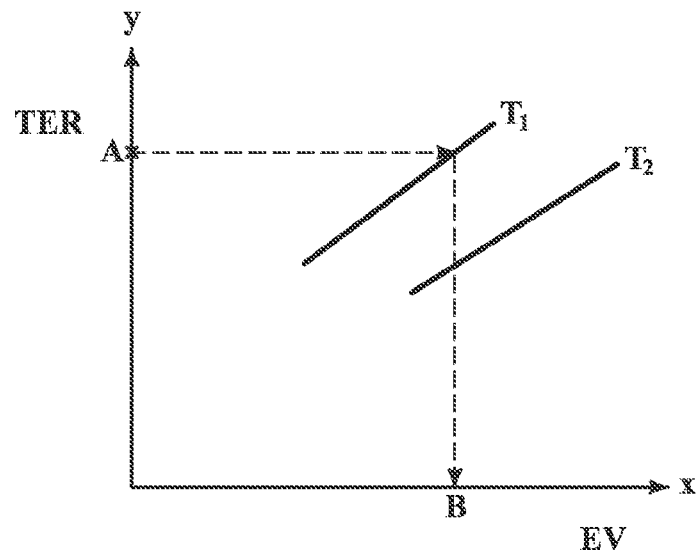
FIG. 14 is a plot of equilibrium volume of a liquid on a slide versus total evaporation rate of the liquid in accordance with an embodiment of the disclosed technology.

FIG. 14 is a plot of equilibrium volume versus total evaporation rate of a processing liquid in accordance with an embodiment of the present technology. The x-axis represents the equilibrium volume (EV, unit: μL), and the y-axis represents the total evaporation rate (TER, unit: μL/s). Lines T1 and T2 represent the relationships between the TER and the EV at temperature T1 and temperature T2, respectively. In the illustrated embodiment, T1 is higher than T2. The controller 144 can receive the total evaporation rate information from the memory 629, the input device 628, or the like. The total evaporation rate information can be measured and stored in the memory 629. The total evaporation rate information can include evaporation rates for liquids at different concentrations. After the controller 144 receives the predetermined temperature (e.g., T1) and the total evaporation rate information (e.g., "A" μL/s), the controller 144 can determine the EV value (e.g., "B" μL) of the liquid based on the graph of FIG. 14. Equation 1 corresponds to the relationships described in FIG. 14. The slope of the lines T1 and T2 represent the temperature-dependent evaporation constant (K) below.

$$TER = K \times EV \quad \text{Equation 1}$$

Once the equilibrium volume of the liquid is determined, the controller 144 can compare it with an estimated volume of the slide and can instruct the dispenser 622 to supply supplemental fluid if needed. If the current volume of the liquid is lower than the target equilibrium volume, the controller 144 can instruct the dispenser 622 to provide more supplemental liquid.

Figure 15:
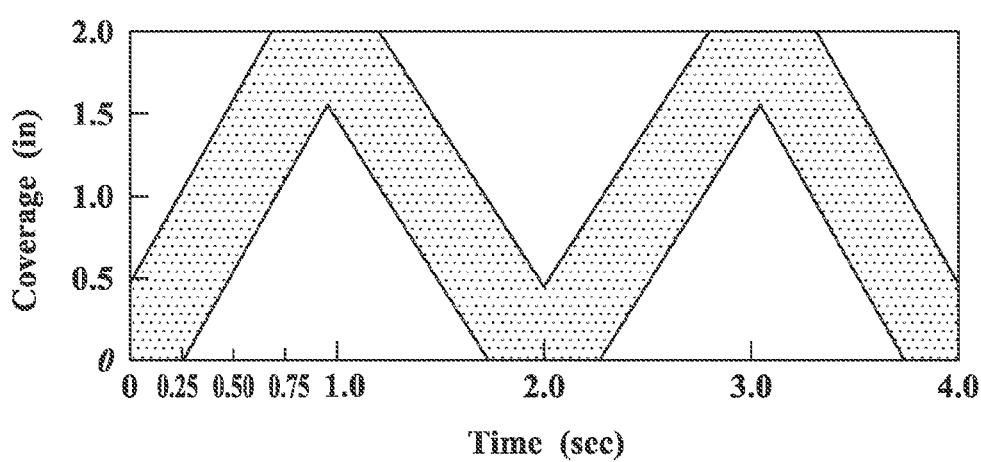
FIG. 15 is a plot of time versus liquid coverage in accordance with an embodiment of the disclosed technology.

FIG. 15 is a plot of time versus coverage of a slide in accordance with an embodiment of the disclosed technology. FIGS. 16A-20B illustrate one method of achieving the coverage depicted in FIG. 15 by moving the liquid 802 along the entire staining area 671 (excluding a label 907 and some margin, if desired) to provide full coverage by being alternatingly moved between opposing ends 732, 735 of the mounting area 671. The full coverage can help minimize, limit, or substantially prevent problems associated with under-wetting and over-wetting. In under-wetting, the liquid 802 contacts less than the entire staining area 671 such that the specimen 807 may be at risk of not being contacted and thus not being treated/stained. In over-wetting, the liquid 802 contacts more than the entire staining area 671 and may tend to drain from the slide 243. The liquid 802 may be at risk of ineffective liquid removal in subsequent processes, resulting in reagent carryover and associated stain quality degradation. If the liquid 802 is a stain, the entire specimen 807 is contacted for consistent (e.g., uniform) staining. If the liquid 802 is a wash, full coverage ensures that the entire specimen 807 is thoroughly washed, especially after a reagent treatment. Different stages of the method are discussed in detail below.

FIGS. 16A and 16B are side and top views of the band of liquid 802 between the opposable 810 held by the opposable actuator (not shown) and the mounting area end 732 at time 0 in FIG. 15. The opposable 810 and slide 243 form a band of liquid 802 (e.g., a meniscus layer, a thin film, or the like). The band of liquid 802 of FIG. 16B is shown in phantom line. A gap 930 (e.g., a capillary gap) can have a minimum holding capacity of about 30 microliters to about 350 microliters. Other minimum and maximum holding capacities are possible, if needed or desired and are dependent upon the gap height, opposable radius, fluid properties, and movement speed. The minimum holding capacity can be the smallest volume of liquid that can be contained in the gap 930 and effectively applied to the specimen 807, which may be located anywhere on the staining area 671. The maximum holding capacity is the largest volume of liquid that can be contained in the gap 930 without loss of fluid control, e.g., spilling of fluid over the side edge or outside of the fluid target areas. The varying height gap 930 can accommodate a wider range of liquid volumes than a uniform height gap because the narrowed region of the gap 930 can accommodate a small liquid volume.

The opposable 810 is rolled along the slide 243 to displace the band of liquid 802 (indicated by an arrow 961) in the direction of a longitudinal axis 951 of the slide 243. In FIGS. 17A and 17B, the band of liquid 802 has been spread by moving a side 958 of the band of liquid 802 in the direction of the longitudinal axis 951 (corresponding to 0.25 seconds in FIG. 15). A side 956 of the band of liquid 802 can remain at an edge 960 of the slide 243. In some embodiments, the band of liquid 802 can be spread from a narrowed width $W_{N1}$ (FIG. 16B) to a spread width $W_S$. The widths $W_{N1}$, $W_S$ can be substantially parallel to the longitudinal axis 951 of the slide 243, and the length L of the band of liquid 802 can be substantially perpendicular to the longitudinal axis 951.

FIGS. 18A and 18B show the band of liquid 802 after it has moved along the slide 243, corresponding to 0.5 second in FIG. 15. The band of liquid 802 is displaced using capillary action. Capillary action can include, without limitation, movement of the band of liquid 802 due to the phenomenon of the liquid spontaneously creeping through the gap 930 due to adhesive forces, cohesive forces, and/or surface tension. In some embodiments, the width $W_S$ can be generally maintained while displacing the band of liquid 802. In other embodiments, the width $W_S$ may be increased or decreased less than 5% while moving the band of liquid 802. In some embodiments, the opposable 810 can have a non-uniform curvature or configuration to have a variable width $W_S$ as the band moves across the slide.

FIGS. 19A and 19B show the band of liquid 802 positioned at the end 735, corresponding to 0.75 second in FIG. 15. The side 958 of the band of liquid 802 can be captivated between an end 952 of the opposable 810 and the end 735 of the mounting area 671. The label 907 can help captivate the liquid 802. For example, the label 907 can be made, in whole or in part, of a hydrophobic material. As the opposable 810 moves to an over-rolled position of FIG. 20A, the width Ws of the band of liquid 802 can be decreased to a narrowed width $W_{N2}$, corresponding to 1 second in FIG. 15. The width of the band of liquid 802 can be reduced while captivating substantially all of the liquid 802 at an end 970 of the gap 930. For example, at least 90% by volume of the liquid 802 can remain captivated. In some embodiments, at least 95% by volume of the liquid 802 can remain captivated. In yet further embodiments, substantially all of the liquid 802 can remain captivated as the width of the band of liquid 802 is decreased.

The compressed width $W_{N2}$ can be substantially less than the width $W_S$ such that the entire narrowed band of liquid 802 is spaced apart from the specimen 807. In some embodiments, the narrowed width $W_{N2}$ can be equal to or less than about 50%, 25%, or 10% of the width $W_S$. Such embodiments may be especially well suited to process slides carrying one or more specimens. A relatively large area of the staining area 671 is uncovered by the narrowed band while preventing wicking or escape of the liquid. In some embodiments, the width $W_{N2}$ can be equal to or less than about 40%, 30%, or 20% of the width W. The width $W_{N1}$ can be generally equal to the width $W_{N2}$. Advantageously, the opposable actuator 525 can be operated to increase or decrease to provide variable narrowing of the band of liquid 802.

The opposable 810 of FIGS. 20A and 20B can be rolled back across the slide 243 to move the band of liquid 802 to the position shown in FIG. 16A. The opposable 810 can be rolled back and forth any number of times at a variable rate or constant rate to move the liquid 802 back and forth across the slide 243. If the liquid 802 is a washing liquid, the washing liquid can be rapidly passed back and forth across the specimen 807 to provide thorough washing. If the liquid 802 is a stain, the band of liquid 802 can be passed back and forth across the specimen 807 to provide uniform staining across an entire width $W_{spec}$ (measured in a direction parallel to the longitudinal axis 951 of the slide 243) of the specimen 807. One or more wash cycles can be performed between staining cycles. On-slide mixing can also be performed, if needed or desired.

Processing protocols may require different rolling speeds and different liquid volumes in order to meet various processing criteria (e.g., chemical requirements, uptake requirements, solubility limitations, viscosity, or the like). If the specimen 807 is a paraffin embedded specimen, a relatively small volume of de-waxing solution (e.g., 12 microliters of xylene) can be delivered into the gap 930. The opposable 810 can be rolled (e.g., rolled along an imaginary plane spaced apart from the upper surface of the slide 243, rolled along the upper surface, rolled sideways, rolled longitudinally, or the like) or otherwise manipulated (e.g., rotated, translated, or both) to apply the liquid 802. After dewaxing, a relatively large volume of reagent can be delivered into the gap 930. For example, a volume of about 125 microliters to about 180 microliters of stain can be delivered into the gap 930. The stain is delivered to the specimen 807 and then subsequently removed.

The method shown in FIGS. 16A-20B can be used to perform assay steps (e.g., antibody and chromogen assays). The assay steps can be performed at relatively low temperatures. The slide holder platen 601 can keep the specimen and/or processing liquid at a temperature in a range of about 35° C. to about 40° C. In one embodiment, the liquid and/or specimen is kept at a temperature of about 37° C. The dispenser (e.g., dispenser 622 of FIG. 13) can deliver supplemental liquid to maintain a target volume of about 30 to about 350 microliters. In some protocols, the dispenser delivers supplemental liquid at a rate of about 4 to about 5.1 microliters per minute to about 5.6 microliters per minute. In such embodiments, the volume of the liquid (e.g., liquid 802 of FIG. 10) can be kept in a range of about 90 microliters to about 175 microliters over about a 15 minute period based on a relative humidity of about 10%-90%, an ambient temperature of about 15° C. to about 32° C., with an average slide temperature tolerance of about ±1° C., and an opposable rolling speed of about 25 to 60 millimeters per second. The evaporation rate may be generally proportional to the rolling speed. If the rolling speed is about 20 millimeters per second, a replenish rate of about 3.8 microliters per minute to about 4.2 microliters per minute can maintain a volume of about 115 microliters to about 200 microliters. If the rolling speed is about 40 millimeters per second, a replenish rate of about 5.1 microliters per minute to about 5.6 microliters per minute can maintain a volume of the liquid 802 of about 115 microliters to about 200 microliters. At a high rolling speed of about 90 millimeters per second, the replenish rate can be about 7.6 microliters per minute to about 8.4 microliters per minute to maintain a volume of about 110 microliters to about 200 microliters. Higher speed may be possible but are dependent upon the gap height, opposable radius, and fluid properties. Humidity and ambient temperatures can impact evaporation rates at low temperatures but may not have a significant impact at elevated temperatures of, for example, temperatures greater than 72° C.

For targeted retrieval, the rolling speed can be about 100 millimeters per second and the replenish rate can be 72 microliters per minute. For antigen retrieval, the rolling speed can be about 180 millimeters per second and the replenish rate can be about 105 microliters per minute. Other replenish rates can be selected based on the processing conditions.

As used herein, the term "opposable element" is a broad term and refers to, without limitation, a surface, a tile, a strip, or another structure capable of manipulating one or more substances to process a specimen on a slide, as described herein. In some embodiments, the opposable element can include one or more spacers, gapping elements or other features for positioning the opposable element relative to a slide. As discussed above, opposable elements can be moved relative to a stationary slide to manipulate a fluid. In other embodiments, a slide is moved relative to a stationary opposable element to manipulate a fluid. In yet other embodiments, both a slide and an opposable element are moved to manipulate a fluid. The opposable 810 (FIGS. 16A and 16B) and opposable 2012 (FIG. 28) are a non-limiting exemplary opposable elements and are discussed in detail in connection with FIGS. 21-38.

FIGS. 21-34 shows one embodiment of the opposable 810. The opposable 810 can include a body 1459, a port 1374, and a slot 1356. The body 1459 includes a first row of gapping elements 1450, a second row of gapping elements 1452, and a specimen processing region 1453. When the specimen processing region 1453 faces a slide and interfaces with or engages a liquid, the liquid can be removed via the port 1374. The slot 1356 can receive a feature of an opposable actuator. The body 1459 can also include keying features 1362, 1364 (e.g., holes, protrusions, etc.) used to align the opposable 810. The illustrated features 1362, 1364 are holes.

Figure 21:
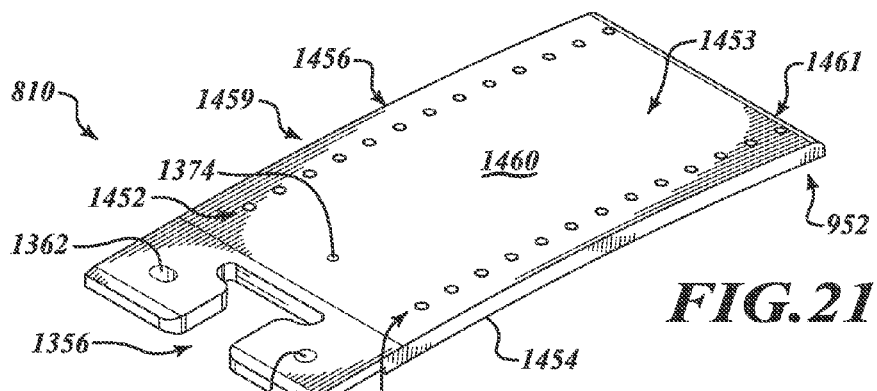
FIG. 21 is an isometric view of an opposable in accordance with one embodiment of the disclosed technology.

FIG. 21 shows the specimen processing region 1453 between the two rows of gapping elements 1450, 1452. The opposable 810 has edges 1454, 1456 that can be dimensioned with respect to the slide to provide the desired processing region 1453 (e.g., the entire surface 1460 of the opposable 810, most of the upper surface 1460 of the opposable 810, the region between the gapping elements 1450, 1452, or the like).

Figure 22:
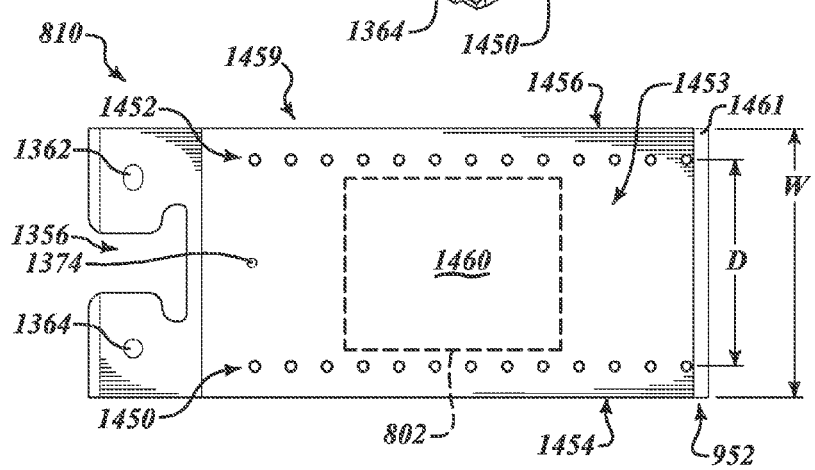
FIG. 22 is a top plan view of the opposable of FIG. 21.

FIG. 22 shows en exemplary band of liquid 802 (illustrated in phantom line) positioned between the gapping elements 1450, 1452. The band of liquid 802 can move along the length of the opposable 810 without contacting the gapping elements 1450, 1452. The band of liquid 802 can be displaced without accumulation of liquid about any of the gapping elements 1450, 1452.

The gapping elements 1450, 1452 can help process a specimen with a desired amount of fluid (e.g., a minimal amount of fluid). The gapping elements 1450, 1452 can also be spaced apart from one another to reduce, limit, or substantially prevent wicking between adjacent elements. If the liquid 802 reaches one of the gapping elements 1450, 1452, the liquid 802 can reside at the contact interface between that gapping element and the slide without flowing to an adjacent gapping element. The gapping elements 1450, 1452 are spaced apart from the edges 1454, 1456 of the opposable 810 to keep the liquid proximate to the processing region 1453. Additionally, the liquid 802 is kept far enough away from the edges 1454, 1456 to prevent wicking out from underneath the opposable 810 even if another object contacts the edges 1454, 1456.

The rows of gapping elements 1450, 1452 extend longitudinally along a length of the opposable 810. Opposing gapping elements of each row of gapping elements 1450, 1452 are generally laterally aligned such that a slide can contact laterally aligned gapping elements 1450, 1452. As the opposable 810 is moved along the slide, the slide is successively brought into contact with laterally aligned gapping elements 1450, 1452.

Each of the rows of gapping elements 1450, 1452 can be generally similar to one another. Accordingly, the description of one of the rows of gapping elements 1450, 1452 applies equally to the other, unless indicated otherwise. The row of gapping elements 1450 can include about 5 gapping elements to about 60 gapping elements with an average distance between adjacent gapping elements in a range of about 0.05 inch (1.27 mm) to about 0.6 inch (15.24 mm). In some embodiments, including the illustrated embodiment of FIGS. 21 and 22, the row of gapping elements 1450 includes 19 gapping elements that protrude outwardly from the entire surface 1460. In other embodiments, the row of gapping elements 1450 includes about 10 gapping elements to about 40 gapping elements. As viewed from above (see FIG. 22), the row of gapping elements 1450 has a generally linear configuration. In other embodiments, the row of gapping elements 1450 has a zigzag configuration, serpentine configuration, or any other configuration or pattern.

The gapping elements 1450 can be evenly or unevenly spaced from one another. The distance between adjacent gapping elements 1450 can be greater than the heights of the gapping elements 1450 and/or less than a thickness T (FIG. 24) of the body 1459 of the opposable 810. Other spacing arrangements are also possible, if needed or desired. In some embodiments, the thickness T is about 0.08 inch (2 mm). A width W between the edges 1454, 1456 can be in a range of about 0.6 inch (15.24 mm) to about 1.5 inch (38 mm). In some embodiments, the width W is about 1.2 inches (30 mm) and the edges 1454, 1456 can be substantially parallel. Other widths are also possible.

Referring to FIG. 22, a distance D between the rows 1450, 1452 can be selected based on the dimensions of the specimen and the dimensions of the slide. In some embodiments, the distance D is in a range of about 0.25 inch (6.35 mm) to about 1 inch (25 mm). If the slide is a standard microscope slide, the distance D can be less than about 0.5 inch (12.7 mm).

Figure 24:
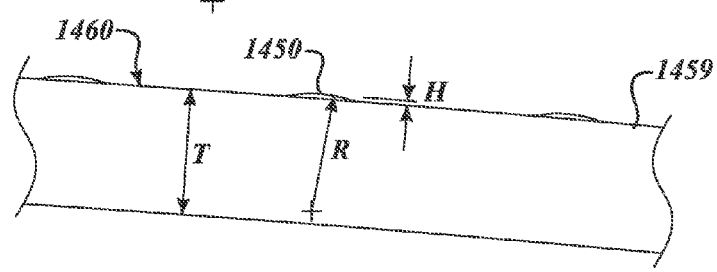
FIG. 24 is a detailed view of a portion of the opposable of FIG. 23.

FIG. 24 shows one of the gapping elements 1450. The height H of the gapping element 1450 can be selected based on the ability to manipulate fluid. The gapping element 1450 can have a height H equal to or less than about 0.0015 inch (0.038 mm) if the specimen is a tissue section with a thickness that is less than about 0.0015 inch (0.038 mm). The minimum height of the capillary gap (e.g., gap 930 of FIGS. 16A-16B) can be equal to 0.0015 inch (0.038 mm) if the gapping elements 1450 contact the slide. In some embodiments, the height H is in a range of about 0.001 inch (0.025 mm) to about 0.005 inch (0.127 mm). In certain embodiments, the height H is about 0.003 inch (0.076 mm) (e.g., 0.003 inch±0.0005 inch) to process thin tissue sections with a thickness less than about 30 microns, 20 microns, or 10 microns.

The pattern, number, dimensions, and configurations of the gapping elements 1450, 1452 can be selected based on the desired interaction between the specimen and the liquid. If the opposable 810 includes a field of gapping elements, the gapping elements can be distributed evenly or unevenly across the opposable 810 to form different patterns that may include, without limitation, one or more rows, arrays, geometric shapes, or the like.

The gapping element 1450 can be a partially spherical dimple, partially elliptical dimple, or the like. The illustrated gapping element 1450 is a substantially partially spherical dimple. If the specimen is sufficiently large or moves towards one side of the slide, the gapping element 1450 in the form of a dimple can slide over the specimen without damaging or dislodging the specimen to the slide. In other embodiments, the gapping element 1450 can be in the form of a polyhedron protrusion, a conical protrusion, a frustoconical protrusion, or another combination of polygonal and arcuate shapes.

Figure 23:
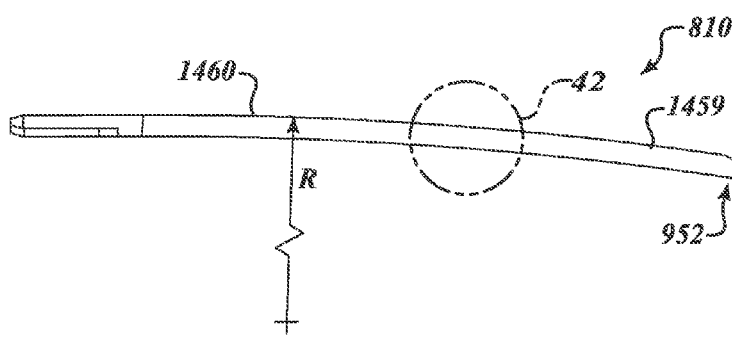
FIG. 23 is a side elevational view of the opposable of FIG. 21.

The body 1459 of FIG. 23 is in the shape of a simple arc with a radius of curvature R in a range of about 2 inches (5 cm) to about 30 inches (76 cm). In some embodiments, the radius of curvature R is about 15 inches (38 cm) or about 20 inches (74 cm). The nominal radius of the profile deviation can be equal to or less than about 0.1 inch. The actual radius of the profile can deviate less than about 0.01 inch. Such embodiments are well suited to produce a liquid band having a generally rectangular shape, as viewed from above, and also spanning the width of the slide and, for a particular volume, having a low variance in length along the slide. The radius of curvature R can be selected based on the number of specimens to be processed, the amount of fluid agitation, the properties of the processing liquids, the height of gapping elements 1450, 1452, and the like. In other embodiments, the opposable 810 is in the shape of a complex arc (e.g., an elliptical arc), a compound arc, or the like. In yet other embodiments, the opposable 810 can be substantially planar. The surface across the width W can be generally straight.

The opposable 810 can be made, in whole or in part, of polymers, plastics, elastomers, composites, ceramics, glass, or metals, as well as any other material that is chemically compatible with the processing fluids and specimen. Exemplary plastics include, without limitation, polyethylene (e.g., high density polyethylene, linear low density polyethylene, blends, or the like), polyvinylidene fluoride (PVDF), polytetrafluoroethylene (PTFE), perfluoroalkoxy (PFA), or combinations thereof. In some embodiments, the opposable 810 can be made of a single material. In other embodiments, different portions of the opposable 810 are made of different materials. If the opposable 810 is disposable, it can be made, in whole or in part, of a relatively inexpensive material. If the opposable 810 is rigid, it can be made, in whole or in part, of polycarbonate, urethane, polyester, a metal coated plate, or the like.

Referring again to FIG. 23, the end 952 includes a captivation feature in the form of a tapered region 1461. The tapered region 1461 is positioned to captivate the band of liquid. As the opposable 810 is over-rolled, the band of liquid can contact and cling to the tapered region 1461. A curved surface 1463 provides a large surface area to which the liquid can cling. The illustrated tapered region 1461 has a radius of curvature equal to or less than about 0.08 inch to cooperate with a standard microscope slide to captivate a band of liquid. Other radii of curvature can also be used, if needed or desired. In some embodiments, the curvature of the rounded edge 1461 is uniform across the width W of the opposable 810. In other embodiments, the curvature of the rounded edge varies across the width W of the opposable 810.

The opposable 810 can be disposable to prevent cross-contamination. As used herein, the term "disposable" when applied to a system or component (or combination of components), such as an opposable element, a processing liquid, or the like, is a broad term and generally means, without limitation, that the system or component in question is used a finite number of times and is then discarded. Some disposable components, such as an opposable element, are used only once and are then discarded. In some embodiments, multiple components of a processing apparatus are disposable to further prevent or limit carryover contamination. In other embodiments, the components are non-disposable and can be used any number of times. For example, opposable elements that are non-disposable may be subjected to different types of cleaning and/or sterilization processes without appreciably altering the characteristics of the opposable element.

It is expected that when a volume of fluid on the surface of a slide advances longitudinally in response to capillary forces, currents within the fluid will predominantly align with the direction of movement rather than become randomly oriented. As such, the relevant fluid dynamics may correspond more to a laminar flow regime than to a turbulent flow regime. In a laminar flow regime, lateral mixing (e.g., mixing generally perpendicular to the direction of movement) may be relatively limited. When a volume of fluid is advanced at relatively high speed along a slide using the opposable, the fluid's inertia can cause some of the fluid to flow past the edges of the slide. Although a rough or a textured surface in contact with the fluid can also induce some increased turbulence and increased lateral mixing, it can also cause bubbles to form in the fluid, which can be undesirable, especially in the context of staining reactions.

When a volume of fluid advanced over a slide includes a reactant (e.g., an oxidizing agent, a chromogen, or another suitable histochemical reactant) that is consumed via interaction with a specimen, limited lateral mixing within the fluid may cause undesirable inhomogeneities in the concentration of the reactant. For example, a specimen can have a non-uniform surface area or density of reaction sites across the width of a slide, which can cause a reactant to be depleted at different rates within different regions of a volume of fluid advanced over the slide. Diffusional mixing alone may be inadequate to equilibrate these inhomogeneities. For example, many reactants have relatively high molecular weights and diffuse relatively slowly such that lateral diffusion may be insufficient to equilibrate the concentration of such reactants. Some specimen-processing reactions are highly dependent on reactant concentration. In dynamic fluid protocols, when different regions of a volume of fluid (e.g., a bolus of fluid, a thin film of fluid, etc.) advanced over a specimen have different reactant concentrations, corresponding regions of the specimen can be processed at different rates, resulting in non-uniform specimen processing (e.g., non-uniform staining of a specimen). This can be problematic when relatively uniform specimen processing is desirable. The non-uniform staining is often in the form of a non-random pattern (e.g., a striped pattern) associated with directionality of the fluid movement. In static fluid processing (e.g., incubation), variations in tissue characteristics may lead to processing irregularities. However, such irregularities may result in processing inconsistencies that are significantly less than processing inconsistencies associated with dynamic fluid staining protocols.

Figure 25:
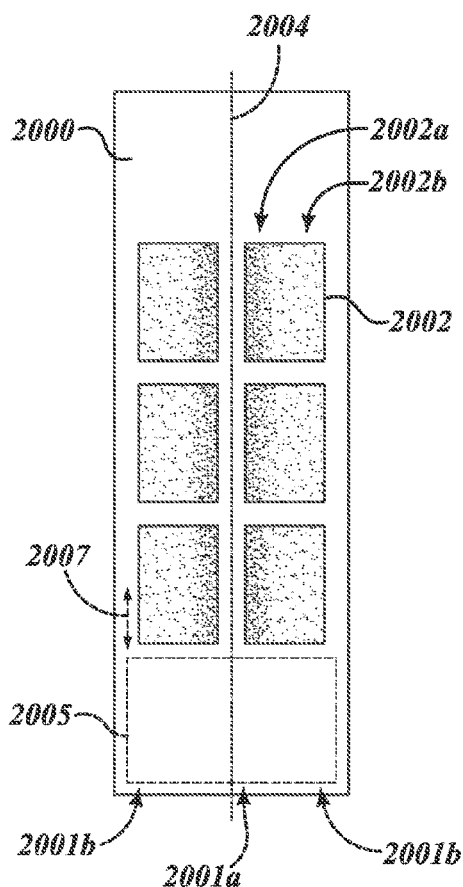
FIG. 25 is a plan view of a specimen-bearing slide illustrating an example of stain non-uniformity.

One example of non-uniform staining is illustrated in FIG. 25, which is a plan view of a slide 2000 and six rectangular specimens 2002 (one identified) positioned on a surface of the slide 2000. The specimens 2002 are spaced apart from one another and generally symmetrically distributed relative to a bisecting plane 2004. The bisecting plane 2004 extends along the centerline of the slide 2000 and is generally parallel to the length of the slide 2000. Inner regions 2002*a* (one identified in FIG. 25) of the specimens 2002 are closer to the bisecting plane 2004 than outer regions 2002*b* (one identified) of the specimens 2002. A volume of fluid 2005 (shown in dashed line) can be moved over the slide 2000. For example, the volume of fluid 2005 can be moved longitudinally (indicated by arrow 2007) along the slide 2000. The inner regions 2002*a* may develop greater stain intensities than the outer regions 2002*b*. Without wishing to be bound by theory, it is possible that a lack of reaction sites around the bisecting plane 2004 (e.g., the lack of reaction sites in the gaps between laterally adjacent specimens 2002) can cause a localized increase in reactant concentration in a portion of the volume of fluid proximate the bisecting plane 2004 relative to portions of the fluid 2005 further from the bisecting plane 2004. For example, a concentration of the reactant at an inner region 2001a of the fluid 2005 can be greater than a concentration of the reactant at outer regions 2001b of the fluid 2005. This concentration difference can cause the non-uniform staining illustrated in FIG. 25.

Figure 26:
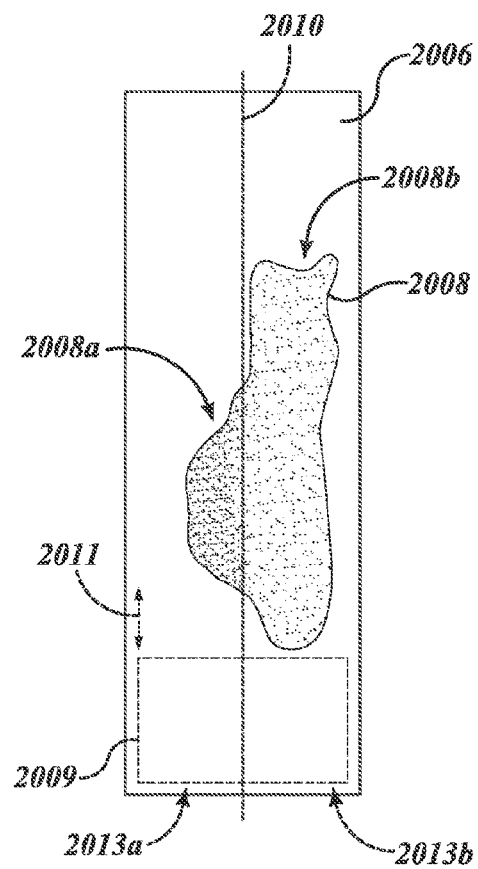
FIG. 26 is a plan view of a specimen-bearing slide illustrating another example of stain non-uniformity.

Another example of non-uniform staining is illustrated in FIG. 26, which is a plan view of a slide 2006 and one irregularly shaped specimen 2008 positioned on a surface of the slide 2006. The specimen 2008 is not symmetrical relative to a bisecting plane 2010. In particular, a first region 2008a of the specimen 2008 on one side of the bisecting plane 2010 is smaller than a second region 2008b of the specimen 2008 on the other side of the bisecting plane 2010. After advancing a volume of fluid 2009 (shown in dashed line) longitudinally over the slide 2006 in the directions indicated by arrow 2011, the first region 2008a may develop greater stain intensity than the second region 2008b. Again, without wishing to be bound by theory, it is possible that a smaller number of reaction sites associated with the first region 2008a relative to the second region 2008b can cause a portion 2013a of the fluid 2009 advanced over the first region 2008a to develop a higher reactant concentration than a portion 2013b of the fluid advanced over the second region 2008b, and that this concentration difference can cause the non-uniform staining illustrated in FIG. 26. In still other examples, natural variation in the number and/or type of reaction sites associated with a specimen can cause non-uniform staining even when the specimen is symmetrical relative to a bisecting plane or other reference plane. Other phenomena can also lead to non-uniform staining similar to or different than the non-uniform staining illustrated in FIGS. 25 and 26.

Figure 27:
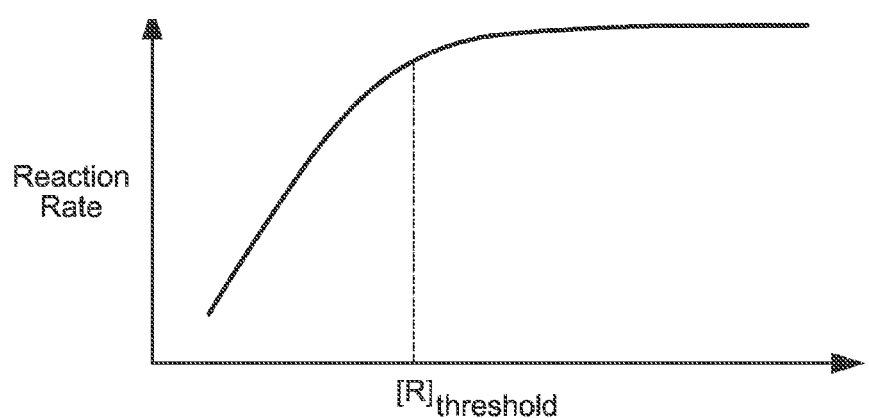
FIG. 27 is a plot of average real-time reactant concentration on the x-axis versus reaction rate on the y-axis for one example of a specimen-processing reaction during a processing period.

FIG. 27 is a plot of average real-time reactant concentration on the x-axis versus reaction rate on the y-axis for one example of a specimen-processing reaction during a processing period (e.g., while a volume of fluid including a reactant is advanced over a specimen). During the processing period, the specimen-processing reaction gradually consumes the reactant. With many specimen-processing reactions, there is a threshold reactant concentration ($[R]_{threshold}$) above which the reaction is zero order (i.e., generally independent of the reactant concentration) and below which the reaction is not zero order (e.g., first or second order). Thus, in some cases, even if a reactant concentration is depleted to produce varying concentration levels within different portions of a volume of fluid, the reaction rate at different regions of the specimen can remain generally the same so long as the depleted levels remain above $[R]_{threshold}$. Various factors, however, such as reactant cost, solubility, poisoning (e.g., enzyme poisoning), and selectivity, among others, can make it technically challenging and/or undesirable to use relatively high initial reactant concentrations. Thus, the initial reactant concentration within a volume of fluid is often insufficient to prevent the real-time reactant concentration in different portions of the fluid from falling below $[R]_{threshold}$ during a processing period. Furthermore, the number of reaction sites associated with a specimen, the size of the specimen, the distribution of the reaction sites, and other factors that affect reactant depletion often vary widely between specimens and may be impractical to control. Specimens can vary, for example, from a single needle biopsy having an area of about 0.01 square centimeters and relatively low antigen loading to a slice of tissue having an area of about 10 square centimeters and relatively high antigen loading. Lateral mixing of a volume of fluid can facilitate generally uniform processing of single needle biopsies, slices of tissue, and other types of specimens. Opposables can be configured to laterally mix a volume of fluid.

FIGS. 28, 29, and 30 are, respectively, an isometric view, a top plan view, and a side elevational view of an opposable 2012 configured in accordance with an embodiment of the present technology. FIG. 31 is a detailed view of a portion of the opposable 2012. In some cases, the opposable 2012 can provide lateral mixing to at least partially compensate for one or more of the phenomena described above and/or other phenomena associated with non-uniform staining. For example, enhanced lateral mixing in accordance with some embodiments of the present technology can facilitate generally even distribution of a reactant throughout a volume of fluid before, during, or after performing a specimen-processing reaction. Furthermore, enhanced lateral mixing can be useful for achieving uniform temperatures, see Table 1) and concentration profiles throughout a volume of liquid, for increasing rinsing efficiency, for increasing homogenization of fluids after replenishing (e.g., after supplementing the fluids to at least partially compensate for evaporation), and/or for enhancing other suitable processes.

TABLE 1

| 30 Second Intervals | | Slide Temp Variation (Degrees C.) Point 1 | Slide Temp Variation (Degrees C.) Point 2 |
| --- | --- | --- | --- |
| Opposable with Uniform Spacer Height | Std Dev % CV | 0.6 0.6 | 0.7 0.8 |
| Opposable with Varying Spacer Height | Std Dev % CV | 0.3 0.4 | 0.3 0.3 |

Referring to FIGS. 28-31, the opposable 2012 can include a non-planar (e.g., arcuate and/or cambered) body 2014 having a fluid-manipulating surface 2016. The opposable 2012 can further include a first spacer 2018 at a first side portion 2016a of the fluid-manipulating surface 2016, and a second spacer 2020 at a second side portion 2016b of the fluid-manipulating surface 2016. In some embodiments, the first and second spacers 2018, 2020 include, respectively, first and second pluralities of discrete protrusions 2022 (individually identified as 2022a-z). The protrusions 2022, for example, can be spaced-apart gapping elements, bumps, points, ridges, dams, walls, or other suitable spacing structures.

The fluid-manipulating surface 2016 can include a central or processing region 2016c between the first and second side portions 2016a, 2016b. For example, the first and second side portions 2016a, 2016b can be spaced apart from one another on either side of a bisecting plane 2024 (FIG. 29). The bisecting plane 2024 can extend through the central region 2016c, be centrally positioned relative to the width of the fluid-manipulating surface 2016, and be generally parallel to the length of the opposable 2012. In some embodiments, the width of the fluid-manipulating surface 2016 extends across generally the entire distance between the edges 1454, 1456. In other embodiments, the width of the fluid-manipulating surface 2016 can extend across only a portion of the distance between the edges 1454, 1456. The body 2014 can be flexible or rigid at the fluid-manipulating surface 2016, and can be made of a molded polymer or another suitable molded or non-molded material.

Figure 32:
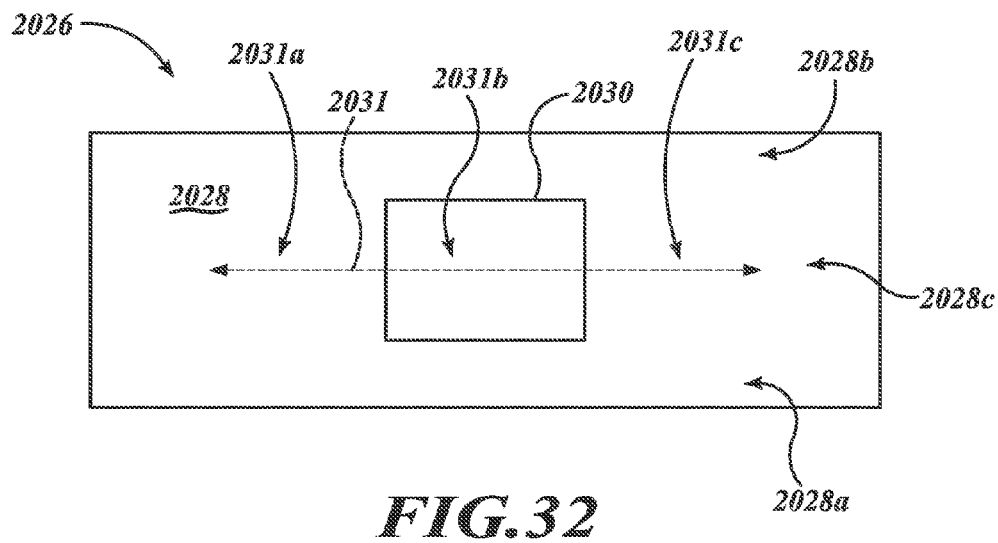
FIG. 32 is a plan view of a slide suitable for use with the opposable of FIG. 28.

FIG. 32 is a plan view of a slide 2026 suitable for use with the opposable 2012. The slide 2026 can include a specimen-bearing surface 2028 having a first side portion 2028a generally corresponding to the first side portion 2016a of the fluid-manipulating surface 2016, a second side portion 2028b generally corresponding to the second side portion 2016b of the fluid-manipulating surface 2016, and a central region 2028c generally corresponding to the central region 2016c of the fluid-manipulating surface 2016. A specimen 2030 can be positioned on the central region 2028c of the specimen-bearing surface 2028. With reference to FIGS. 28-32 together, the opposable 2012 and the slide 2026 can be configured to be positioned proximate to one another with the first spacer 2018 at least partially in contact with the first side portion 2028a, and the second spacer 2020 at least partially in contact with the second side portion 2028b.

The opposable 2012 and the slide 2026 can be configured to form a fluid-carrying gap (not shown) between a portion of the central region 2016c of the fluid-manipulating surface 2016 and a corresponding portion of the central region 2028c of the specimen-bearing surface 2028. The central region 2016c can be curved to facilitate controlled manipulation of a fluid (not shown) within the fluid-carrying gap by rolling action (e.g., rolling capillary action). In this way, fluid can be advanced along a processing path 2031 (FIG. 32) extending over the specimen 2030. The fluid can be advanced cyclically, such as from a first end portion 2031a of the processing path 2031, over a middle portion 2031b of the processing path 2031, to a second end portion 2031c of the processing path 2031, and then back over the middle portion 2031b to the first end portion 2031a. The central region 2016c can have a radius of curvature R (FIGS. 30 and 31) from about 2 inches (5.2 cm) to about 30 inches (76.2 cm), from about 10 inches (25.4 cm) to about 20 inches (50.8 cm), or within another suitable range. In some embodiments, R is about 15 inches (38.1 cm). The portions of the central regions 2016c, 2028c forming the fluid-carrying gap can be centered or off-center relative to the bisecting plane 2024. In some embodiments, the fluid-carrying gap is spaced apart from the first spacer 2018 and/or the second spacer 2020. In other embodiments, the fluid-carrying gap can extend to, through, or past the first spacer 2018 and/or the second spacer 2020.

Figure 33:
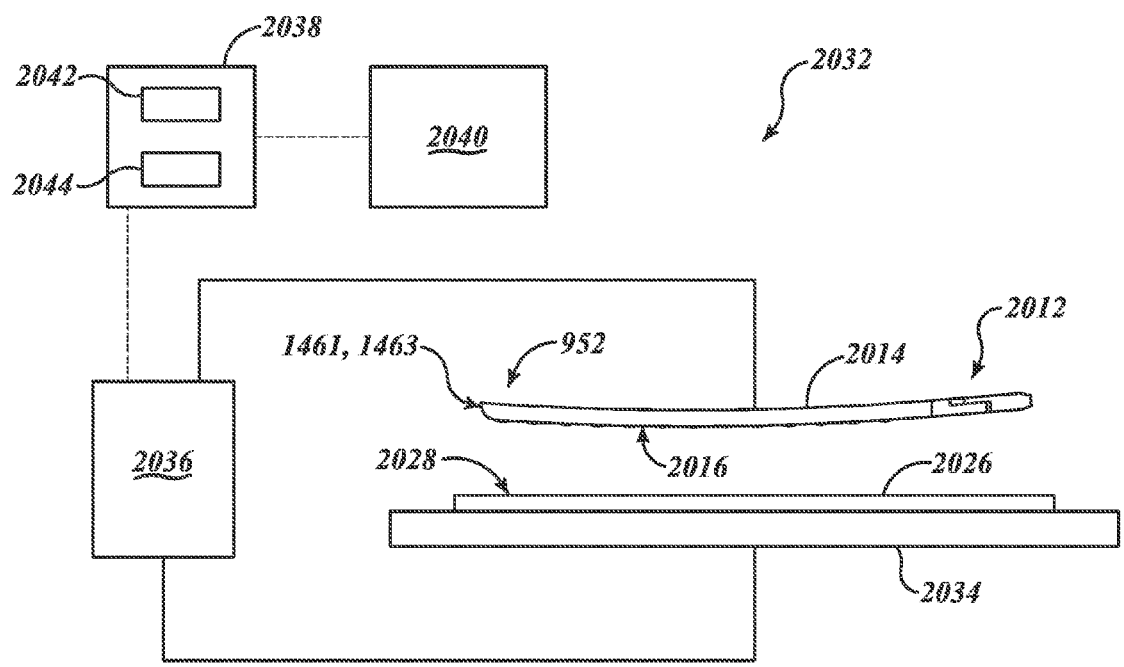
FIG. 33 is a partially schematic side elevational view of a specimen-processing assembly including the opposable of FIG. 28 and loaded with the slide of FIG. 32 in accordance with an embodiment of the disclosed technology.

FIG. 33 is a partially schematic side elevational view of a specimen-processing assembly 2032 including the opposable 2012 and a platen 2034 configured to support the slide 2026. The opposable 2012 and the slide 2026 (e.g., via the platen 2034) can be configured to interact via a fluid-manipulating action to change the portions of the central regions 2016c, 2028c forming the fluid-carrying gap (e.g., to advance the fluid-carrying gap over the length of the slide 2026). The fluid-manipulating action can include, for example, rotating the opposable 2012 relative to the slide 2026, rotating the slide 2026 relative to the opposable 2012, or both, in a plane of rotation (not shown).

The specimen-processing assembly 2032 can include an actuator 2036 operably connected to the opposable 2012 and to the platen 2034. In other embodiments, the actuator 2036 can be operably connected to the opposable 2012 only, to the platen 2034 only, or have another suitable configuration. The actuator 2036 can be configured to move (e.g., rotate or tilt) the opposable 2012 relative to the platen 2034, to move (e.g., rotate, tilt, etc.) the platen 2034 relative to the opposable 2012, or both, in the plane of rotation. The plane of rotation can be, for example, a plane generally parallel to (e.g., the same as) the bisecting plane 2024 (FIG. 29). The specimen-processing assembly 2032 can further include a controller 2038 operably connected to the actuator 2036, and a user interface 2040 operably connected to the controller 2038. The controller 2038 can include a processor 2042 and memory 2044 and can be programmed with instructions (e.g., non-transitory instructions, a sequence of instructions, etc.) that, when executed, cause the actuator 2036 to carry out the fluid-manipulating action.

With reference to FIGS. 28-33 together, the first and second spacers 2018, 2020 can be configured to vary the profile or cross section of the fluid-carrying gap (e.g., a profile or cross section of the fluid-carrying gap in a direction transverse to the length of the slide 2026) to provide enhanced lateral mixing. In some embodiments, the first and second spacers 2018, 2020 change the orientation of the fluid-manipulating surface 2016 relative to the slide 2026 to produce lateral flows in the volume of fluid. Pairs of protrusions 2022 on opposite sides of the opposable 2012 can have different heights to alter the tilt of at least a portion of the opposable 2012 relative to the slide 2026. In this or another suitable manner, the first and second spacers 2018, 2020 can differentially space apart the first and second side portions 2016a, 2016b of the fluid-manipulating surface 2016 from the first and second side portions 2028a, 2028b of the specimen-bearing surface 2028, respectively, during the fluid-manipulating action. The first spacer 2018 can have a first height profile parallel to the plane of rotation and the second spacer 2020 can have a second height profile parallel to the plane of rotation different than the first height profile. As different protrusions 2022 come into contact with the first and second side portions 2028a, 2028b, respectively, the difference between the first and second height profiles can change the shape of the fluid-carrying gap and thereby cause fluid within the fluid-carrying gap to move laterally. This lateral movement can cause, for example, chaotic advection that can at least partially mitigate the poor lateral mixing often associated with laminar flow regimes.

In some embodiments, the first and second height profiles can include a step down and a step up, respectively, toward the edge 1461 (FIG. 28). For example, the protrusions 2022h-s can have a first height $H_1$ (FIG. 31) and the protrusions 2022a-g and 2022t-z can have a second height $H_2$ (FIG. 31), with $H_1$ being less than $H_2$. $H_1$ can be, for example, from about 0.001 inch to about 0.004 inch, from about 0.002 inch to about 0.0035 inch, or within another suitable range. In some embodiments, $H_1$ is about 0.003 inch. $H_2$ can be, for example, from about 0.004 inch to about 0.008 inch, from about 0.005 inch to about 0.007 inch, or within another suitable range. In some embodiments, $H_2$ is about 0.006 inch. A ratio of $H_1$ to $H_2$ can be, for example, from about 1:1.25 to about 1:3, from about 1:1.5 to about 1:2.5, or within another suitable range. In some embodiments, the ratio of $H_1$ to $H_2$ is about 1:2. Other suitable values for $H_1$, $H_2$, and the ratio of $H_1$ to $H_2$ are also possible. Furthermore, other suitable height profiles are possible. For example, the first height profile, the second height profile, or both can change gradually rather than abruptly. As another example, the first height profile, the second height profile, or both can include more than one height gradient. As yet another example, the first height profile, the second height profile, or both can allow the first side portions 2016a, 2028a to touch while second side portions 2016b, 2028b are spaced apart and/or allow the second side portions 2016b, 2028b to touch while first side portions 2016a, 2028a are spaced apart during at least a portion of the fluid-manipulating action.

Figure 34A:
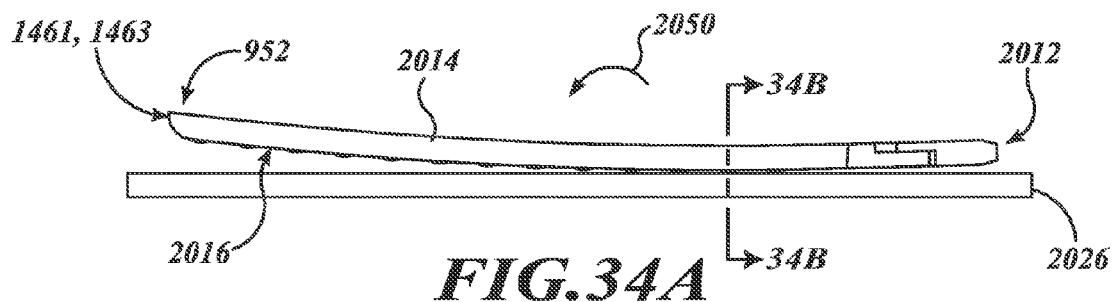
FIG. 34A is a side elevational view of the opposable of FIG. 28 and the slide of FIG. 32 in a first end state.
Figure 34B:
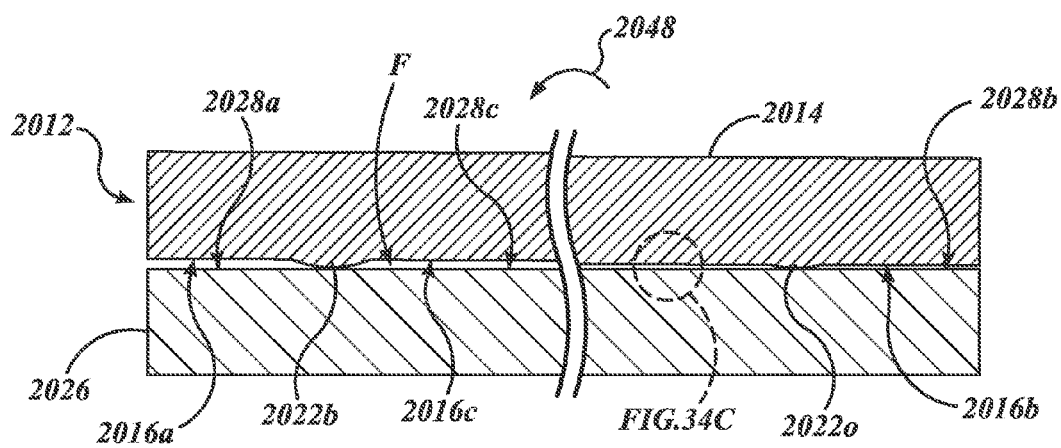
FIG. 34B is a cross-sectional view taken along line 34B-34B in FIG. 34A.
Figure 34C:
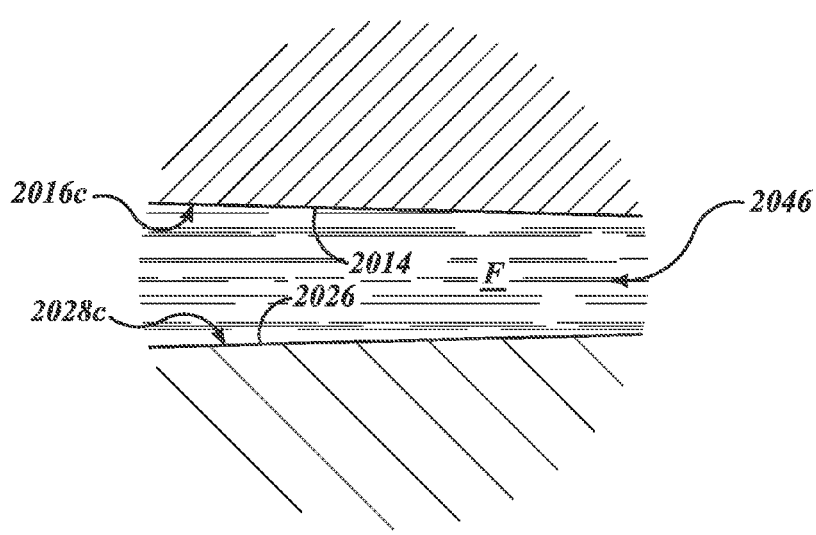
FIG. 34C is an enlarged view of a fluid-carrying gap of FIG. 34B with exaggerated slope.
Figure 35A:
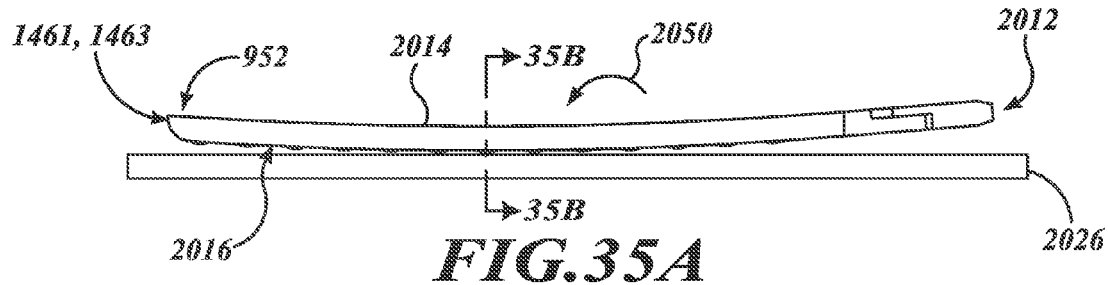
FIG. 35A is a side elevational view of the opposable of FIG. 28 and the slide of FIG. 32 in an intermediate state.
Figure 35B:
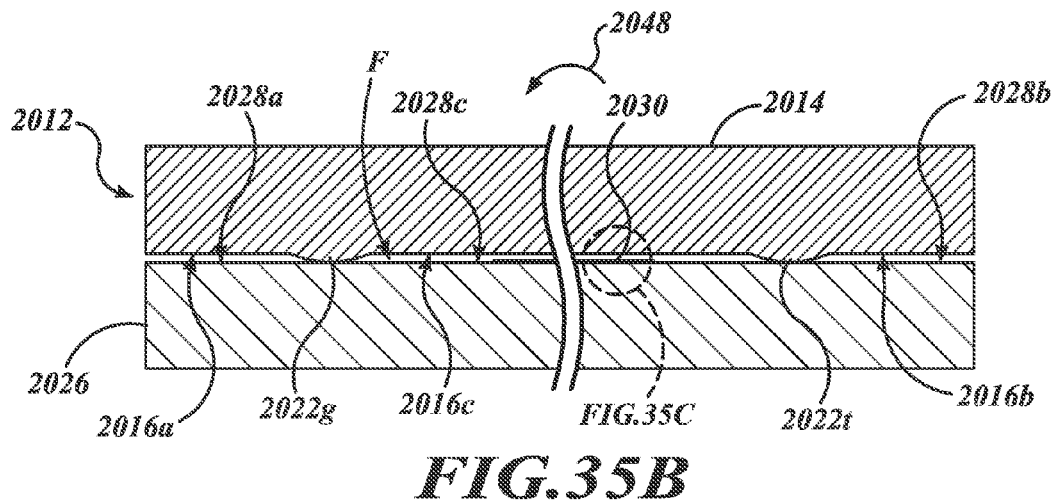
FIG. 35B is a cross-sectional view taken along line 35B-35B in FIG. 35A.
Figure 35C:
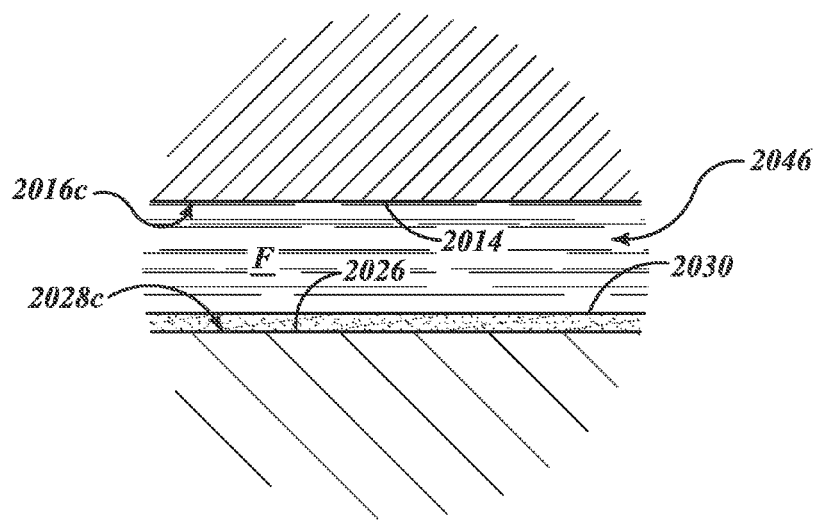
FIG. 35C is an enlarged view of a fluid-carrying gap of FIG. 35B.
Figure 36A:
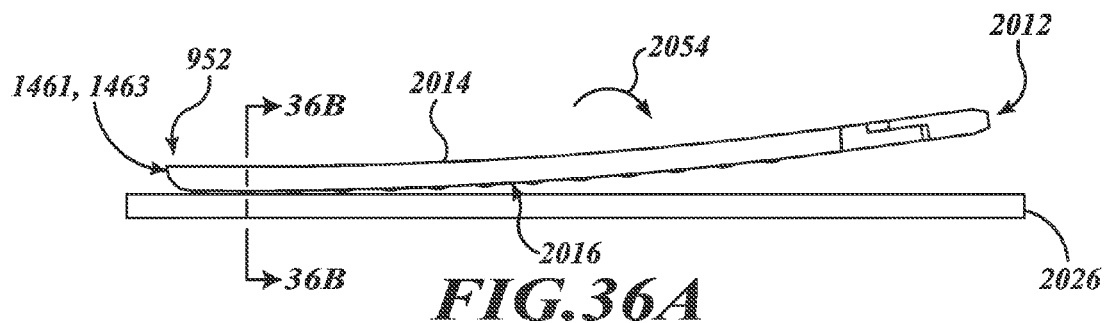
FIG. 36A is a side elevational view of the opposable of FIG. 28 and the slide of FIG. 32 in a second end state.
Figure 36B:
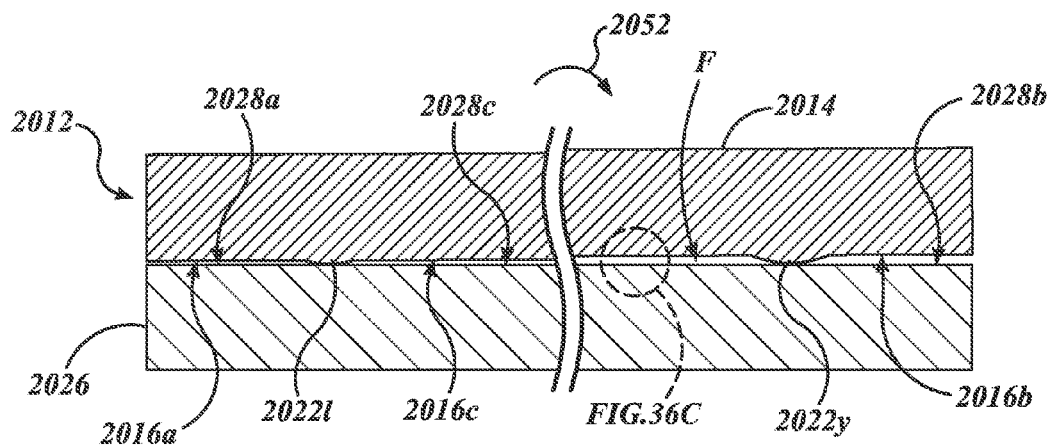
FIG. 36B is a cross-sectional view taken along line 36B-36B in FIG. 36A.
Figure 36C:
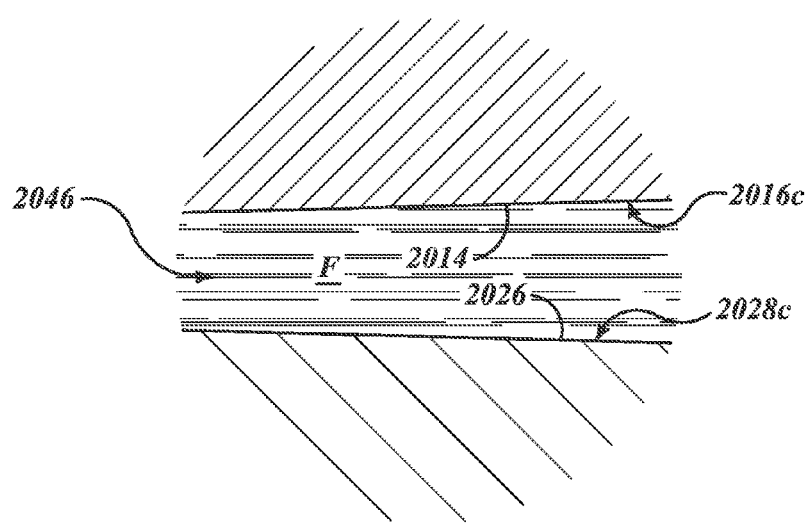
FIG. 36C is an enlarged view of a fluid-carrying gap of FIG. 36B with exaggerated slope.

The opposable 2012 and the slide 2026 can be moved from a first end state to a second end state and through a range of intermediate states between the first and second end states. FIGS. 34A, 35A, and 36A are side elevational views of the opposable 2012 and the slide 2026 at the first end state, at an intermediate state within the range of intermediate states, and at the second end state, respectively. FIGS. 34B, 35B, and 36B are cross-sectional views taken along line 34B-34B in FIG. 34A, along the line 35B-35B in FIG. 35A, and along the line 36B-36B in FIG. 36A, respectively. FIGS. 34C, 35C, and 36C are enlarged views of a fluid-carrying gap 2046 formed by the opposable 2012 and the slide 2026 in the first end state, the intermediate state, and the second state, respectively, with exaggerated slope shown in FIGS. 34C and 36C. In some cases, the opposable 2012 can be in a rolling position in the intermediate states and in an over roll or turnaround position in one or both of the first and second end states.

Referring to FIGS. 34A-36C together, moving from the first end state to the second end state and through the range of intermediate states can cause different portions of the first and second spacers 2018, 2020 come into and out of contact with the first and second side portions 2028a, 2028b of the specimen-bearing surface 2028, respectively. For example, at the first end state (FIGS. 34A-C), a first portion of the first spacer 2018 (e.g., protrusions 2022a-d) and a first portion of the second spacer 2020 (e.g., protrusions 2022n-q) can be in contact with the specimen-bearing surface 2028. At the second end state (FIGS. 36A-C), a second portion of the first spacer 2018 (e.g., protrusions 2022j-m) and a second portion of the second spacer 2020 (e.g., protrusions 2022w-z) can be in contact with the specimen-bearing surface 2028. Within the range of intermediate states (one shown in FIGS. 36A-C), a third portion of the first spacer 2018 (e.g., protrusions 2022e-i) and a third portion of the second spacer 2020 (e.g., protrusions 2022r-v) can be in contact with the specimen-bearing surface 2028. The first and second portions of the first spacer 2018 can be spaced apart along the first side portion 2016a of the fluid-manipulating surface 2016 with the third portion of the first spacer 2018 positioned therebetween. Similarly, the first and second portions of the second spacer 2020 can be spaced apart along the second side portion 2016b of the fluid-manipulating surface 2016 with the third portion of the second spacer 2020 positioned therebetween.

During the fluid-manipulating action, the first and second spacers 2018, 2020 can cause at least a portion of the fluid-manipulating surface 2016 to rotate in a plane that is not parallel to the plane of rotation (e.g., a plane generally perpendicular to the plane of rotation). For example, the opposable 2012 can rock in the lateral direction or tilt from side to side as it is rolled along the slide 2026. In some cases, the fluid-manipulating action includes moving the opposable 2012 and/or the slide 2026 in opposite directions within the plane of rotation. This can reverse the movement of fluid within the fluid-carrying gap 2046 along the processing path 2031 (FIG. 32) as well as reverse lateral movement of the fluid caused by the first and second spacers 2018, 2020. For example, the first and second spacers 2018, 2020 can be configured to cause at least a portion of the fluid-manipulating surface 2016 to rotate in a first direction 2048 (FIGS. 34B and 35B) while the opposable 2012 rotates relative to the slide 2026 in a second direction 2050 (FIGS. 34A and 35A) different than the first direction 2048 and the opposable 2012 and the slide 2026 move from the first end state toward the second end state. Similarly, the first and second spacers 2018, 2020 can be configured to cause at least a portion of the fluid-manipulating surface 2016 to rotate in a third direction 2052 (FIG. 36B) while the opposable 2012 rotates relative to the slide 2026 in a fourth direction 2054 (FIG. 36A) different than the third direction 2052 and the opposable 2012 and the slide 2026 move from the second end state toward the first end state. In some embodiments, the first and third directions 2048, 2052 are generally opposite and/or the second and fourth directions 2050, 2054 are generally opposite.

The transverse cross section of the fluid carrying gap 2046 can vary as the opposable 2012 moves to different positions. The transverse cross sections of the fluid carrying gap 2046 can be wedge shaped, triangular shaped, or have other suitable configurations to provide an asymmetrical flow channel. For example, the flow channel can have an asymmetrical cross section when the opposable 2012 moves towards the over rolled position (FIG. 36A) and a symmetrical cross section when the opposable 2012 is in an intermediate position (FIG. 35A). In some cases, lateral mixing can be performed primarily at one or both turnaround portions of the rolling motion. In other cases, lateral mixing can be performed relatively consistently throughout the rolling motion. The overall geometry of the flow channel (e.g., the three-dimensional space through which the fluid-carrying gap 2046 moves during the fluid-manipulating action) can have various suitable shapes, such as shapes that have generally equal volumes on either side of the bisecting plane 2024 (FIG. 29) and shapes that have different volumes on either side of the bisecting plane 2024. In some embodiments, at least a portion of the flow channel can have a substantially saddle shape, partially spherical shape, partially frusto-conical shape, generally triangular shape or wedge shape, or the like. Different portions of the flow channel can have different shapes. Different portions of the opposable 2012 can have non-planar configurations (e.g., saddle shaped, partially spherical shape, partially frusta-conical shape, etc.), planar configurations, or the like to define such flow channels.

In some embodiments, the first and second spacers 2018, 2020 can be configured to cause a cross section of the fluid-carrying gap 2046 in a first plane perpendicular to the plane of rotation (e.g., a plane corresponding to line 34B-34B in FIG. 34A) to have a first asymmetry relative to the bisecting plane 2024 (FIG. 29) when the opposable 2012 and the slide 2026 are in the first end state. Similarly, the first and second spacers 2018, 2020 can be configured to cause a cross section of the fluid-carrying gap 2046 in a second plane perpendicular to the plane of rotation (e.g., a plane corresponding to line 36B-36B in FIG. 36A) to have a second asymmetry relative to the bisecting plane 2024 when the opposable 2012 and the slide 2026 are in the second end state. The first and second asymmetries can be generally opposite relative to one another. The first asymmetry can correspond to a volumetric taper of the fluid-carrying gap 2046 in a first direction toward the first spacer 2018, and the second asymmetry can correspond to a volumetric taper of the fluid-carrying gap 2046 in a second direction toward the second spacer 2020. The changing volumetric taper of the fluid-carrying gap 2046 can cause fluid (and reactants) within the fluid-carrying gap 2046 to move in a direction opposite to the direction of the volumetric taper due to displacement and/or to move in the direction of the volumetric taper due to capillary action. For clarity purposes, the fluid is not shown in FIGS. 34B, 35B, 36B, although the fluid can be located at fluid gap F. Both types of movement can enhance lateral mixing of the fluid. The changing volumetric taper of the fluid-carrying gap 2046 can also have other additional and/or alternative effects on the fluid within the fluid-carrying gap 2046 that can enhance lateral mixing of the fluid and/or have other benefits.

The height profiles of the spacers 2018, 2020 can be selected to cause generally even lateral mixing of fluid in opposite directions. For example, the height profiles of the spacers 2018, 2020 on opposite sides of the opposable can be different. This can cause a lateral mixing effect that occurs when the opposable 2012 moves from the first state to the second state to be generally reversed when the opposable 2012 and the slide 2026 move from the second state back to the first state. When the first portion of the first spacer 2018 has an average height greater than that of the first portion of the second spacer 2020, and the second portion of the first spacer 2018 has an average height less than that of the first portion of the second spacer 2020, an average height of the first and second portions together of the first spacer 2018 can be about equal to an average height of the first and second portions together of the second spacer 2020. An average height of the third portion of the first spacer 2018 can also be about equal to an average height of the third portion of the second spacer 2020. These attributes can facilitate generally symmetrical volumetric distribution relative to a plane (e.g., a bisecting plane not shown) perpendicular to the bisecting plane 2024 (FIG. 29). Furthermore, they can cause the fluid-carrying gap 2046 to be relatively symmetrical while it passes over the central region of the slide 2026, which carries the specimen 2030. This can increase the volumetric consistency of portions of the fluid proximate different regions of the specimen 2030.

As discussed above, enhanced lateral mixing can facilitate more uniform staining of specimens. For example, in at least some enzymatic staining reactions, enhanced lateral mixing can allow for acceptable levels of stain uniformity across a broad range of specimen variation without using initial reactant concentrations high enough to poison the enzyme. In one illustrative example, the specimen 2030 (FIG. 32) can have different antigen loads on opposite sides of a bisecting plane (not shown) parallel to the processing path 2031. The antigen load on one side of the bisecting plane can be, for example, from about 50% to about 500%, from about 100% to about 300%, or within another suitable range greater than the antigen load on the other side of the bisecting plane.

The opposable 2012 can be used to advance a fluid including a reactant (e.g., an oxidizing agent, such as hydrogen peroxide) along with another reactant (e.g., a chromogen, such as 3,3'-diaminobenzidine) over the specimen 2030. The fluid can be advanced, for example, at a speed from about 10 millimeters/second to about 40 millimeters/second, from about 20 millimeters/second to about 30 millimeters/second, or within another suitable range. In some cases, the fluid is advanced at a speed of about 25 millimeters/second. The fluid can have a volume, for example, from about 50 microliters to about 250 microliters, from about 75 microliters to about 125 microliters, or within another suitable range. In some cases, the fluid has a volume of about 100 microliters. The concentration of one or both of the reactants can be from about 100% to about 300%, from about 100% to about 200%, or within another suitable range of a minimum concentration for generally maintaining an enzymatic staining reaction at zero order. When the reactant is an oxidizing agent (e.g., hydrogen peroxide), higher concentrations of the reactant can, in some cases, poison enzymes (e.g., horseradish peroxidase) bound to the antigens on the specimen 2030 via antibodies.

The opposable 2012 can also be used to perform on slide mixing, a feature heretofore not possible with flat surface capillary gap systems. In one embodiment, a small volume of a concentrated reagent or reagent in a storage buffer is aspirated into a reagent pipette from a vial. This reagent is transported to, and dispensed on, the slide. A larger volume of a diluent fluid is dispensed through the pipette onto the slide to dilute the reagent and provide the bulk of the fluid to satisfy the target volume requirements. It has also been found that the use of a non-buffered fluid can be added to a wide variety of reagents without changing their chemical dynamics. This process can also be used to modify the ratio of chromogen reagents (or other mix ratios) by selectively diluting some components while leaving others at their starting concentration. This process can also be used to enhance intentional stain intensity. For many steps, final stain intensity can be adjusted by modifying the on-slide concentration on the fly. Once the target reagent and dilution volume is on the slide, the opposable can provide mixing of the laminar reagent and diluent providing even distribution over the surface of the slide. Since the reagents applied in this manner are dropped sequentially onto the slide, they form relatively discrete layers on the slide which promotes mixing via the orthogonal movement of the opposable and opposable actuator assembly.

Figure 37:
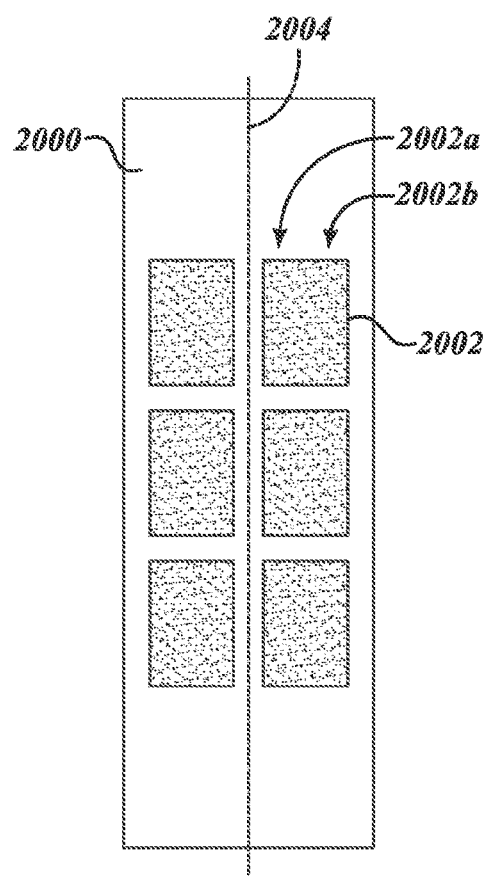
FIG. 37 is a plan view of a specimen-bearing slide illustrating an example of relatively uniform staining in accordance with an embodiment of the disclosed technology.
Figure 38:
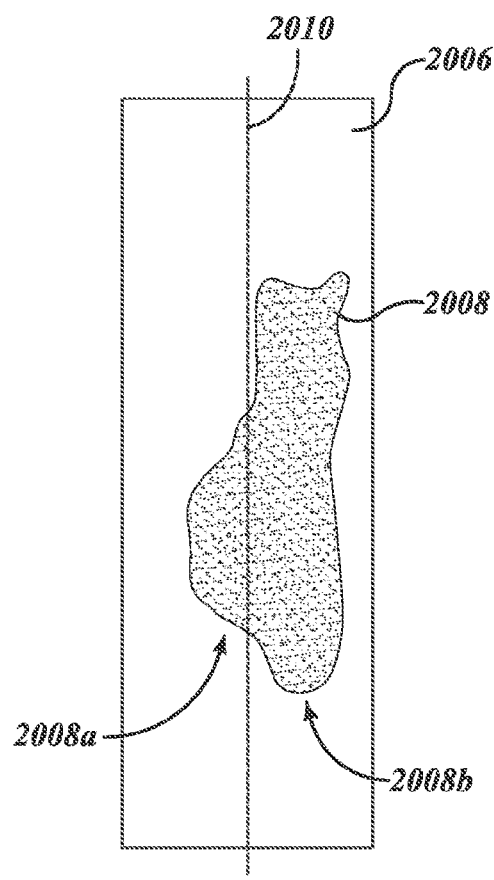
FIG. 38 is a plan view of a specimen-bearing slide illustrating another example of relatively uniform staining in accordance with an embodiment of the disclosed technology.

FIGS. 37 and 38 are plan views of the slides 2000, 2006 with specimens processed with the opposable 2012. In contrast to the stain non-uniformity illustrated in FIGS. 43 and 44, FIGS. 55 and 56 illustrate examples of relatively uniform staining. Due at least in part to enhanced lateral mixing, after staining, the specimens 2002 (FIG. 37) and 2008 (FIG. 38) can have stain-intensity gradients less than about 15%, less than about 10%, or within another suitable range. In some cases, the specimens 2002, 2008 have stain-intensity gradients of about 5% and/or stain-intensity gradients generally undetectable to the naked eye. Other beneficial staining outcomes are also possible. In some embodiments, opposables 2012 can be used with the system 100 to achieve substantially uniform processing across one or more specimen.

The slides disclosed herein can be a 1 inch×3 inch microscope slide, a 25 mm×75 mm microscope slide, or another type of flat or substantially flat substrate. "Substantially flat substrate" refers, without limitation, to any object having at least one substantially flat surface, but more typically to any object having two substantially flat surfaces on opposite sides of the object, and even more typically to any object having opposed substantially flat surfaces, which opposed surfaces are generally equal in size but larger than any other surfaces on the object. In some embodiments, the substantially flat substrate can comprise any suitable material, including plastics, rubber, ceramics, glass, silicon, semiconductor materials, metals, combinations thereof, or the like. Non-limiting examples of substantially flat substrates include flat covers, SELDI and MALDI chips, silicon wafers, or other generally planar objects with at least one substantially flat surface.

From the foregoing, it will be appreciated that specific embodiments of the invention have been described herein for purposes of illustration, but well-known structures and functions have not been shown or described in detail to avoid unnecessarily obscuring the description of at least some embodiments of the invention. The systems described herein can perform a wide range of processes for preparing biological specimens for analyzing. Where the context permits, singular or plural terms may also include the plural or singular term, respectively. Unless the word "or" is associated with an express clause indicating that the word should be limited to mean only a single item exclusive from the other items in reference to a list of two or more items, then the use of "or" in such a list shall be interpreted as including (a) any single item in the list, (b) all of the items in the list, or (c) any combination of the items in the list. The singular forms "a," "an," and "the" include plural referents unless the context clearly indicates otherwise. Thus, for example, reference to "a specimen" refers to one or more specimens, such as two or more specimens, three or more specimens, or four or more specimens.

The various embodiments described above can be combined to provide further embodiments. The embodiments, features, systems, devices, materials, methods, and techniques described herein may, in some embodiments, be similar to any one or more of the embodiments, features, systems, devices, materials, methods, and techniques described in U.S. patent application Ser. No. 13/509,785; U.S. patent application Ser. No. 13/157,231; U.S. Pat. No. 7,468,161; U.S. patent application Ser. No. 13/509,785; U.S. Patent Application No. 61/746,085, filed on Dec. 26, 2012 and entitled AUTOMATED SPECIMEN PROCESSING SYSTEMS AND METHODS OF USING THE SAME; U.S. Patent Application No. 61/746,087, filed on Dec. 26, 2012 and entitled SPECIMEN PROCESSING SYSTEMS AND METHODS FOR MODERATING EVAPORATION, U.S. Patent Application No. 61/746,089, filed on Dec. 26, 2012 and entitled SPECIMEN PROCESSING SYSTEMS AND METHOD FOR UNIFORMLY HEATING SLIDES; and U.S. Patent Application No. 61/746,091, filed on Dec. 26, 2012 and entitled SPECIMEN PROCESSING SYSTEMS AND METHODS FOR ALIGNING SLIDES; and International App. No. PCT/US2010/056752, all of which are incorporated by reference in their entireties. In addition, the embodiments, features, systems, devices, materials, methods, and techniques described herein may, in certain embodiments, be applied to or used in connection with any one or more of the embodiments, features, systems, devices, materials, methods, and techniques disclosed in the above-mentioned International App. No. PCT/US2010/056752; U.S. patent application Ser. No. 13/509,785; U.S. Patent Application No. 61/746,085, filed on Dec. 26, 2012 and entitled AUTOMATED SPECIMEN PROCESSING SYSTEMS AND METHODS OF USING THE SAME; U.S. Patent Application No. 61/746,087, filed on on Dec. 26, 2012 and entitled SPECIMEN PROCESSING SYSTEMS AND METHODS FOR MODERATING EVAPORATION, U.S. Patent Application No. 61/746,089, filed on Dec. 26, 2012 application and entitled SPECIMEN PROCESSING SYSTEMS AND METHOD FOR UNIFORMLY HEATING SLIDES; and U.S. Patent Application No. 61/746,091, filed on Dec. 26, 2012 and entitled SPECIMEN PROCESSING SYSTEMS AND METHODS FOR ALIGNING SLIDES, and U.S. Pat. No. 7,468,161. Aspects of the disclosed embodiments can be modified, if necessary, to employ concepts of the various patents, applications, and publications to provide yet further embodiments.

These and other changes can be made to the embodiments in light of the above-detailed description. For example, a seal element can have a one-piece or multi-piece construction and can include any number of retention features. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A specimen-processing assembly, comprising: a platen configured to support a slide having a specimen-bearing surface;

an opposable including—
 an arcuate body having a fluid-manipulating surface,
 a first spacer at a first side portion of the fluid-manipulating surface, and
 a second spacer at a second side portion of the fluid-manipulating surface, the second side portion being spaced apart from the first side portion, wherein the first and second side portions are generally parallel to the specimen-bearing surface; and
an actuator configured to rotate the opposable relative to the platen, to rotate the platen relative to the opposable, or both in a path of rotation from a first end state at which a first portion of the first spacer and a first portion of the second spacer contact the specimen-bearing surface to a second end state at which a second portion of the first spacer and a second portion of the second spacer contact the specimen-bearing surface; wherein the first portion of the first spacer is spaced apart from the second portion of the first spacer at the first side portion of the fluid-manipulating surface; and the first portion of the second spacer is spaced apart from the second portion of the second spacer at the second side portion of the fluid-manipulating surface; and
wherein the first spacer has a height profile parallel to the specimen-bearing surface different than a height profile of the second spacer parallel to the specimen-bearing surface; and wherein an average height of the first portion of the first spacer is greater than an average height of the first portion of the second spacer; and an average height of the second portion of the first spacer is less than an average height of the second portion of the second spacer.

2. A specimen-processing assembly, comprising: a platen configured to support a slide having a specimen-bearing surface;

an opposable including—
 an arcuate body having a fluid-manipulating surface,
 a first spacer at a first side portion of the fluid-manipulating surface, and
 a second spacer at a second side portion of the fluid-manipulating surface, the second side portion being spaced apart from the first side portion; and
an actuator configured to move the opposable relative to the platen, to move the platen relative to the opposable, or both in a path of rotation from a first end state to a second end state and through a range of intermediate states between the first and second end states, the first and second side portions being generally parallel to the specimen-bearing surface,
wherein the first spacer has a height profile parallel to the specimen-bearing surface different than a height profile of the second spacer parallel to the specimen-bearing surface; the body is configured to form a fluid-carrying gap between a portion of a central region of the fluid-manipulating surface and a corresponding portion of a central region of the specimen-bearing surface; wherein rotating the opposable relative to the platen, rotating the platen relative to the opposable, or both changes the portion of the central region of the fluid-manipulating surface and the corresponding portion of the central region of the specimen-bearing surface forming the fluid-carrying gap; the first and second spacers are configured to cause a cross section of the fluid-carrying gap in a first plane perpendicular to the specimen-bearing surface to have a first asymmetry at the first end state relative to a bisecting plane parallel to the specimen-bearing surface, and to cause a cross section of the fluid-carrying gap in a second plane perpendicular to the specimen-bearing surface to have a second asymmetry relative to the bisecting plane at the second end state; and the first asymmetry is different than the second asymmetry.

3. The specimen-processing assembly of claim 2, wherein:
the first spacer includes a first plurality of discrete protrusions configured to contact the specimen-bearing surface; and
the second spacer includes a second plurality of discrete protrusions configured to contact the specimen-bearing surface.

4. The specimen-processing assembly of claim 2, wherein the first and second spacers are configured to cause at least a portion of the fluid-manipulating surface to perpendicularly rotate relative to the path of rotation while the actuator rotates the opposable relative to the platen, rotates the platen relative to the opposable, or both in the path of rotation.

5. The specimen-processing assembly of claim 2, wherein: the first and second spacers are configured—to cause at least a portion of the fluid-manipulating surface to rotate in a first direction while the actuator rotates the opposable relative to the platen, rotates the platen relative to the opposable, or both in a second direction, and to cause at least a portion of the fluid-manipulating surface to rotate in a third direction while the actuator rotates the opposable relative to the platen, rotates the platen relative to the opposable, or both in a fourth direction; the first, second, third, and fourth directions are different; the first direction is generally opposite to the third direction; and the second direction is generally opposite to the fourth direction.

6. The specimen-processing assembly of claim 2, wherein a section of the height profile of the first spacer and a section of the height profile of the second spacer on opposite sides of the opposable are different.

7. The specimen-processing assembly of claim 2, wherein the actuator is configured to rotate the opposable such that a volume of liquid held between the fluid-manipulating surface and the slide, is translated along the slide.

8. The specimen-processing assembly of claim 1, wherein an average height of the first and second portions together of the first spacer is about equal to an average height of the first and second portions together of the second spacer.

9. The specimen-processing assembly of claim 1, wherein: a radius of curvature of the fluid-manipulating surface in a bisecting plane parallel to the path of rotation is from about 2 inches to about 30 inches; the average height of the first portion of the first spacer and the average height of the second portion of the second spacer individually are from about 0.004 inch to about 0.008 inch; and the average height of the second portion of the first spacer and the average height of the first portion of the second spacer individually are from about 0.001 inch to about 0.004 inch.

10. The specimen-processing assembly of claim 1, wherein an average height of a third portion of the first spacer between the first and second portions of the first spacer is about equal to an average height of a third portion of the second spacer between the first and second portions of the second spacer.

* * * * *